US012773697B2

(12) United States Patent
Cyr et al.

(10) Patent No.: US 12,773,697 B2
(45) Date of Patent: Oct. 27, 2026

(54) DEVICES AND METHODS FOR PARTICLE MIXING

(71) Applicant: IDEXX Laboratories, Inc., Westbrook, ME (US)

(72) Inventors: Jason Cyr, Windham, ME (US); Kevin Chamberland, Portland, ME (US); Jennifer Cote, Wells, ME (US); Arvind Dev, Scarborough, ME (US); Julie Rollins, South Portland, ME (US); Andrey Asanov, Buxton, ME (US)

(73) Assignee: IDEXX LABORATORIES, INC, Westbrook, ME (US)

( * ) Notice: Subject to any disclaimer, the term of this patent is extended or adjusted under 35 U.S.C. 154(b) by 901 days.

(21) Appl. No.: 18/078,531

(22) Filed: Dec. 9, 2022

(65) Prior Publication Data

US 2023/0184754 A1 Jun. 15, 2023

Related U.S. Application Data

(60) Provisional application No. 63/288,378, filed on Dec. 10, 2021, provisional application No. 63/288,408,
(Continued)

(51) Int. Cl.
*G01N 1/10* (2006.01)
*A61J 1/20* (2006.01)
(Continued)

(52) U.S. Cl.
CPC ............... *B01L 9/06* (2013.01); *A61J 1/2096* (2013.01); *A61M 5/1782* (2013.01); *A61M 5/19* (2013.01);
(Continued)

(58) Field of Classification Search
None
See application file for complete search history.

(56) References Cited

U.S. PATENT DOCUMENTS 5,646,049 A 7/1997 Tayi
6,270,249 B1 8/2001 Besuner et al.
(Continued)

FOREIGN PATENT DOCUMENTS

JP 2013 072687 4/2013
WO WO2016168692 A1 10/2016

OTHER PUBLICATIONS

Rong et al., "A Novel Magnetic Chaotic Mixer for In-Flow Mixing of Magnetic Beads", 7th International Conference on Miniaturized Chemical and Biochemical Analysis Systems, Oct. 5-9, 2003, USA, pp. 335-338. (Year: 2003).*
(Continued)

*Primary Examiner* — Rebecca M Giere
(74) *Attorney, Agent, or Firm* — McDonnell Boehnen Hulbert & Berghoff LLP

(57) ABSTRACT

A method for preparing for preparing a solution comprising a plurality of particles in a vial is disclosed. The method includes agitating the vial at a first predetermined mixing speed. The method also includes dispersing, into the vial, during the agitating, a first volume of buffer solution at a first predetermined dispensing rate to suspend the plurality of particles in the solution, wherein particles of the plurality of particles comprise a unique identifying feature.

19 Claims, 17 Drawing Sheets

Related U.S. Application Data filed on Dec. 10, 2021, provisional application No. 63/288,397, filed on Dec. 10, 2021, provisional application No. 63/288,386, filed on Dec. 10, 2021.

(51) Int. Cl.

| | |
|---|---|
| ***A61M 5/178*** | (2006.01) |
| ***A61M 5/19*** | (2006.01) |
| ***B01L 9/00*** | (2006.01) |
| ***B01L 9/06*** | (2006.01) |
| ***G01N 1/08*** | (2006.01) |
| ***G01N 1/28*** | (2006.01) |
| ***G01N 21/88*** | (2006.01) |
| ***G01N 33/543*** | (2006.01) |
| *G01N 1/18* | (2006.01) |

(52) U.S. Cl.

CPC .................. *B01L 9/54* (2013.01); *G01N 1/08* (2013.01); *G01N 1/10* (2013.01); *G01N 1/2806* (2013.01); *G01N 21/8851* (2013.01); *G01N 33/54326* (2013.01); *A61J 2205/10* (2013.01); *B01L 2200/022* (2013.01); *B01L 2200/0605* (2013.01); *B01L 2300/021* (2013.01); *G01N 2001/185* (2013.01)

(56) References Cited

U.S. PATENT DOCUMENTS

| | | | | |
|---|---|---|---|---|
| 10,232,376 | B2 | 3/2019 | Capaccio et al. | |
| 2008/0038559 | A1 | 2/2008 | True | |
| 2009/0293643 | A1 | 12/2009 | Powell et al. | |
| 2011/0098201 | A1 | 4/2011 | Seul et al. | |
| 2011/0152127 | A1 | 6/2011 | Ho | |
| 2011/0159578 | A1 | 6/2011 | Godsey et al. | |
| 2013/0034284 | A1* | 2/2013 | Honkanen | H04N 25/63 382/129 |
| 2014/0274778 | A1* | 9/2014 | Tsao | C40B 30/04 506/14 |
| 2015/0253224 | A1* | 9/2015 | Liffmann | G01N 33/56972 435/40.51 |
| 2016/0289669 | A1* | 10/2016 | Fan | B01L 3/502761 |
| 2020/0164322 | A1* | 5/2020 | Renick | B01F 33/813 |

OTHER PUBLICATIONS

International Search Report and Written Opinion issued in International Application No. PCT/US2022/052374 dated Jul. 21, 2023.

International Search Report and Written Opinion issued in International Application No. PCT/US2022/052375 dated Apr. 14, 2023.

International Search Report and Written Opinion issued in International Application No. PCT/US2022/052376 dated May 19, 2023.

International Search Report and Written Opinion issued in International Application No. PCT/US2022/052377 dated May 19, 2023.

* cited by examiner

DEVICES AND METHODS FOR PARTICLE MIXING

CROSS-REFERENCE TO RELATED APPLICATIONS

This application claims priority to U.S. Provisional Patent Application No. 63/288,378, filed on Dec. 10, 2021, U.S. Provisional Patent Application No. 63/288,408, filed on Dec. 10, 2021, U.S. Provisional Patent Application No. 63/288,397, filed on Dec. 10, 2021, and U.S. Provisional Patent Application No. 63/288,386, filed on Dec. 10, 2021, each of which is hereby incorporated by reference in its entirety. Additionally, this application hereby incorporates by reference the following U.S. Patent Applications, each filed on the same date as the present application: U.S. patent application Ser. No. 18/078,510, titled "Devices and Methods for Pipette Alignment", U.S. patent application Ser. No. 18/078,519, titled "Devices and Methods for Particle Solution Testing" and U.S. patent application Ser. No. 18/078,528, titled "Devices and Methods for Particle Solution Preparation".

FIELD OF THE DISCLOSURE

The present disclosure involves systems and methods for preparing a solution comprising a plurality of particles in a vial. Namely, devices and methods of the disclosure agitate the solution inside the vial at predetermined mixing speed and dispense into the vial, during the agitating, a volume of buffer solution at a predetermined dispensing rate to suspend the plurality of particles in the solution, wherein particles of the plurality of particles comprise a unique identifying feature.

BACKGROUND

Assays (including immunoassays) can be conducted utilizing a variety of different solutions, including solutions containing particles to assist in performing the assays.

SUMMARY

In some examples, paramagnetic beads or polystyrene particles, can be suspended within a solution that can be used for testing and identification of components in the solutions. To increase the accuracy of assay test results, it is desirable to, prior to testing, ensure that the particles are dispersed evenly throughout the solution.

When operators manually prepare the solution for testing, the homogeneity and number of particles throughout the prepared solution may be inconsistent and/or inaccurate. Further, if the operator allows too much time to elapse between manually stirring the solution and withdrawing a sample therefrom, the particles may become less homogenized throughout the solution (e.g., by settling to the bottom of the vessel, clumping together or both, among other potential issues), which in turn can also impact the accuracy and precision of any assay results for which the solution may be used. Accordingly, manual preparations of the solution are subject to variability between preparations and/or operators and, thus, degrade the accuracy and precision of any associated assay results.

In an example, a method is described for preparing a solution comprising a plurality of particles in a vial. The method comprises agitating the vial at a first predetermined mixing speed. The method also comprises dispersing, into the vial, during the agitating, a first volume of buffer solution at a first predetermined dispensing rate to suspend the plurality of particles in the solution, wherein particles of the plurality of particles comprise a unique identifying feature.

In another example, a non-transitory computer-readable medium is described, having stored thereon program instructions that, upon execution by a controller cause a controller to perform a set of operations. The set of operations comprises agitating a vial at a first predetermined mixing speed. The set of operations also comprises dispersing, into the vial, during the agitating, a first volume of buffer solution at a first predetermined dispensing rate to suspend a plurality of particles in the solution, wherein particles of the plurality of particles comprise a unique identifying feature.

The features, functions, and advantages that have been discussed can be achieved independently in various examples or may be combined in yet other examples. Further details of the examples can be seen with reference to the following description and drawings.

BRIEF DESCRIPTION OF THE FIGURES

The above, as well as additional features will be better understood through the following illustrative and non-limiting detailed description of example embodiments, with reference to the appended drawings.

Figure 1:
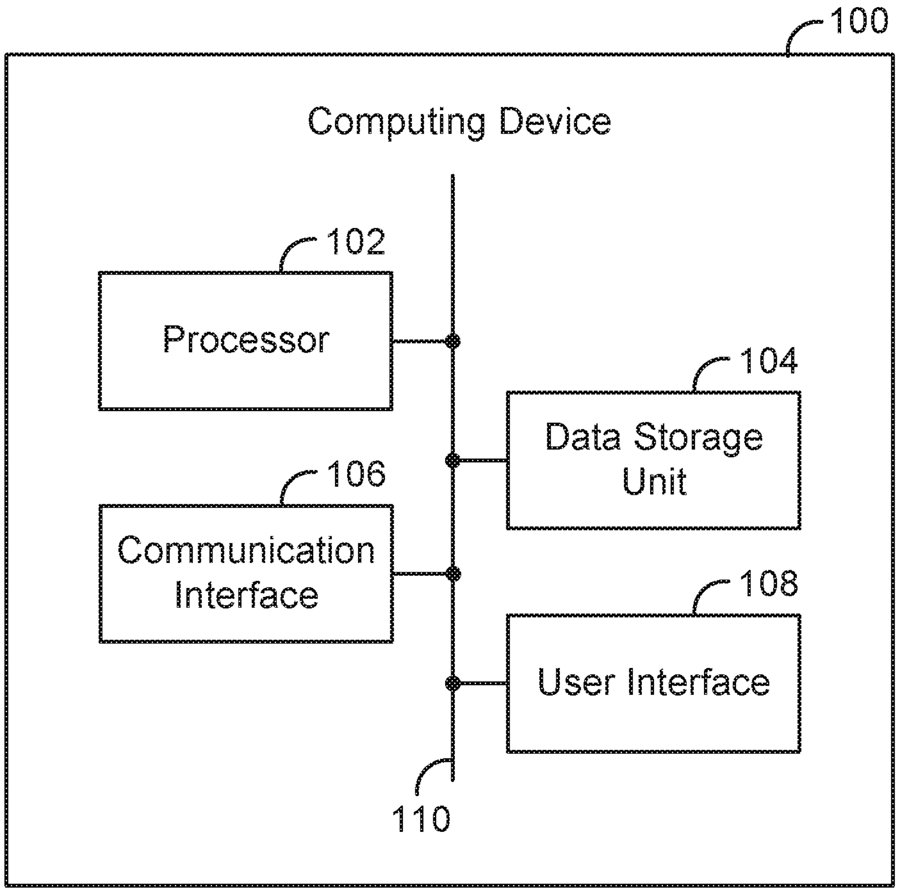
FIG. 1 illustrates a simplified block diagram of an example computing device, according to an example embodiment.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

Within examples, the disclosure is directed to devices and methods for preparing samples of a solution containing one or types of particles utilizing a shaker plate system. In particular, as described in the example embodiments, the one or more types of particles may include one or more of the following: microbeads, microparticles, micropellets, microwafers, paramagnetic beads, microparticles containing one or more identifying features (such as a bar code, a color, a shape, an alphanumeric symbol, and/or the like), paramagnetic microparticles, paramagnetic microparticles containing one or more bar codes, and/or beads containing one or more nickel bar codes. Moreover, the particles may be magnetic or paramagnetic. Particles suitable for use in the disclosure are capable of attachment to other substances such as derivatives, linker molecules, proteins, nucleic acids, or combinations thereof. The capability of the particles to be attached to other substances can result from the particle material as well as from any further surface modifications or functionalization of the particle. The particles can be functionalized or be capable of becoming functionalized in order to covalently or non-covalently attach proteins, nucleic acids, linker molecules or derivatives as described herein.

For example, the surface of the particle can be modified or functionalized with amine, biotin, streptavidin, avidin, protein A, sulfhydryl, hydroxyl and carboxyl. Particles may be spherical or other shapes, may be light transmissive and may be digitally coded such as for example, by an image that provides for high contrast and high signal-to-noise optical detection to facilitate identification of the bead. To the extent an image is present, the image may be implemented by a physical structure having a pattern that is partially substantially transmissive (e.g., transparent, translucent, and/or pervious to light), and partially substantially opaque (e.g., reflective and/or absorptive to light) to light. The pattern of transmitted light is determined (e.g., by scanning or imaging), and the code represented by the image on the coded bead can be decoded. Various code patterns, such as circular, square, or other geometrical shapes, can be designed as long as they can be recognized by an optical decoder. Examples of these one or more types of particles may be found at: U.S. Pat. Nos. 7,745,091, 8,148,139, and 8,614,852.

Additionally or alternatively, the one or more types of particles may comprise one or more materials, including one or more of the following: glass, polymers, polystyrene, latex, elemental metals, ceramics, metal composites, metal alloys, silicon, or of other support materials such as agarose, ceramics, glass, quartz, polyacrylamides, polymethyl methacrylates, carboxylate modified latex, melamine, and Sepharose, and/or one or more hybrids thereof. In particular, useful commercially available materials include carboxylate modified latex, cyanogen bromide activated Sepharose beads, fused silica particles, isothiocyanate glass, polystyrene, and carboxylate monodisperse microspheres. Furthermore, the one or more types of particles may also comprise one or more specific shapes, dimensions, and/or configurations and may be modified for one or more specific uses. For example, the particles may be a variety of sizes from about 0.1 microns to about 100 microns, for example about 0.1, 0.5, 1.0, 5, 10, 20, 30, 40 50, 60, 70, 80 90 or 100 microns. For example, the one or more types of particles may be surface modified and/or functionalized with biomolecules for use in biochemical analysis.

The particles of the disclosure may be used in various homogenous, sandwich, competitive, or non-competitive assay formats to generate a signal that is related to the presence or amount of an analyte in a test sample. The term “analyte,” as used herein, generally refers to the substance, or set of substances in a sample that are detected and/or measured, either directly or indirectly. In various aspects the assays of the disclosure, examples include sandwich immunoassays that capture an analyte in a sample between a binding member (e.g., antibody) attached to the particle and a second binding member for the analyte that is associated with a label. In another example embodiment, the binding member on the particle may be an antigen (e.g., protein) that binds an antibody of interest in a patient sample in order to capture the antibody on the particle. The presence of the antibody can then be detected with a label conjugated to a second binding member specific for an antibody. The second binding member attached to the label may be the antigen conjugated to the label or the binding member may itself be an antibody (e.g., anti-species antibody) that is conjugated the label. In example embodiments, these characteristics may be referred to herein as a “unique identifying feature” of the particle. Other examples are possible. For example, the particle may also bind to a fluorescent tag or label, which may present a “unique identifying feature” of the particle to which the fluorescent tag or label might bind under a fluorescent lighting.

In another example embodiment, the assay methods of the disclosure are competitive immunoassays for detection of antibody in the sample. A competitive immunoassay may be carried out in the following illustrative manner. A sample, from an animal’s body fluid, potentially containing an antibody of interest that is specific for an antigen, is contacted with the antigen attached to the particle and with the anti-antigen antibody conjugated to a detectable label. The antibody of interest, present in the sample, competes with the antibody conjugated to a detectable label for binding with the antigen attached to the particles. The amount of the label associated with the particles can then be determined after separating unbound antibody and the label. The signal obtained is inversely related to the amount of antibody of interest present in the sample.

In an alternative example embodiment of a competitive a sample, an animal’s body fluid, potentially containing an analyte, is contacted with the analyte conjugated to a detectable label and with an anti-analyte antibody attached to the particle. The antigen in the sample competes with analyte conjugated to the label for binding to the antibody attached the particle. The amount of the label associated with the particles can then be determined after separating unbound antigen and label. The signal obtained is inversely related to the amount of analyte present in the sample.

Antibodies, antigens, and other binding members may be attached to the particle or to the label directly via covalent binding with or without a linker or may be attached through a separate pair of binding members as is well known (e.g., biotin: streptavidin, digoxigenin: anti-digoxiginen). In addition, while the examples herein reflect the use of immunoassays, the particles and methods of the disclosure may be used in other receptor binding assays, including nucleic acid hybridization assays, that rely on immobilization of one or more assay components to a solid phase.

Assays using these solutions are often conducted over a series of agitation events. In practice, the particles in the solution may bind together (often referred to as "clumping") or bind and/or settle on the bottom or sides of a vial. This binding may result in an inconsistent dispersion of the particles in the solution. In further examples, during preparation of the solution, one or more components other than the vial may contribute to the binding or clumping of the particles in the vial. For example, the density of the particles may be lower than the density of the solution, which may result in the particles floating to the top of the solution and inconsistent particle dispersion throughout the solution.

In other examples, after one or more binding members have attached to the particles, the solution surrounding the particles may be removed from the vial and the particles with attached binding members (collectively referred to herein as "assembled particles") may be washed in preparation for testing. In an example embodiment, during this washing portion, one or more components may be used to facilitate the washing, including one or more components of the system to secure the assembled particles in the vial. For example, if the assembled particles have magnetic or paramagnetic properties, a magnet may be used to secure the assembled particles in the vial while a washing solution is dispersed into the vial to improve the results of the washing portion (e.g., by ensuring that the assembled particles remain intact and in the vial during a vigorous dispersing event). In this example embodiment, however, by securing the assembled particles in the vial using a magnet, the assembled particles may exhibit one or more undesirable effects prior to testing (e.g., the assembled particles may bind and/or clump together). Other examples are possible.

When these particles clump together, they may not be accurately identified or accounted for in the assay. In another example, the particles bind/settle on the bottom or sides of the vial, which may result in inconsistent and/or inaccurate results in the assay. To help address this issue, a shaker plate system, which typically includes vials coupled to a shaker plate controlled via a programmable controller, can agitate the solution (for example by way of shaking the vials via the shaker plate) before or during a buffer solution dispersing event in order to more consistently disperse the particles in the solution before testing. However, the mixing speed and mixing pattern of the shaker plate and the rate and amount of buffer solution dispersed into the vial during agitation may affect the consistency of the assay results and/or the type and consistency of particles dispersed within the solution.

To help address these issues, a program for controlling the shaker plate system can be utilized to cause the shaker plate and a pipette to perform a preset series of agitation and dispersing events to improve accuracy and consistency of assay results across both vials and tests. Namely, the controller of the shaker plate system can cause the shaker plate and pipettes to execute a series of agitation and dispersing events where the mixing speed of the shaker plate is set to a predetermine rotational velocity, pattern (e.g., orbital, linear, etc.), and/or other parameters. For example, the controller of the shaker plate may cause the shaker plate systems to move in a pattern and/or specific tolerance to ensure that one or more components operate within a specific range of parameters in relation to one another. For example, the controller may cause the shaker plate system to position one or more vials such that a pipette is in the horizontal center of the vials and shake the vials in an orbital pattern in an orbit within a predetermined tolerance of the pipette in relation to the vials from the pipette to the walls of the vial in which the pipette is inserted) (e.g., an orbital patter of up to 3 mm).

In example embodiments, certain mixing speeds and patterns may more consistently agitate the solution, which can lead to consistent dispersion of the particles within the solution, thereby producing more accurate and consistent particle counts than other mixing speeds and patterns.

Additionally, the controller can cause the pipettes to disperse a particular amount of a buffer solution at a predetermined rate, potentially at a predetermined depth within the vial. In example embodiments, the controller may cause the pipettes to dispense a predetermined amount of the buffer solution at a predetermined rate and/or depth within the vial by controlling one or more components of the systems and devices described here (e.g., the pipettes, the shaker plate system, etc.) and/or one subparts thereof (e.g., one or more motors, actuators, and/or other mechanical components of the pipettes, the shaker plate system, etc.). By doing so, the accuracy of particle count and/or type prepared in the solution prior to testing may be improved as compared to systems that do not cause the pipettes to dispense a predetermined amount of the buffer solution at a predetermined rate and/or depth within the vial.

For example, positioning the end of the pipette tip at or near the center or middle of the vial (e.g., the center line of the height of the vial or the "vertical center") may allow the pipette to more effectively disperse the solution into the vial to produce more accurate and consistent particle counts compared to other positions such as the bottom of the vial or the top of the vial. As such, in example embodiments, the controller causes the pipettes to be positioned such that, during a dispersing and/or agitating event, the end of the pipette tip is at or near the vertical and/or horizontal center of the volume of the vial or another particular position.

Similarly, positioning the end of the pipette tip at or near the center or middle of the horizontal cross section of the vial (the "horizontal center") may allow the pipette to more consistently disperse the solution into the vial. As used in this disclosure, horizontal indicates a direction transverse to the vertical direction, and extending outward from a vertical centerline of the referenced body (e.g., the horizontal center of a vial stabilized in one position in a vial receptacle). This specific positioning can produce more accurate and consistent particle counts compared to other positions, such as the side of the vial. As such, in example embodiments, the pipette alignment device and methods described herein position a pipette such that, during an agitating and/or dispensing event, the end of the pipette tip is at near the horizontal center of the vial.

In practice, dispersing events may be performed in a series. For example, a first volume of the buffer solution may be dispersed into the vial, and a first assay read conducted. Then a volume of the buffer solution may be dispersed into the vial, and second assay read conducted. This process may be repeated a number of times, either before a single assay read is conducted or in between several assay reads. Further, these agitation and dispersing events may be performed across multiple vials of solution at once (e.g., eight vials).

Devices and methods of the present disclosure also involve positioning a pipette such that the end of the pipette tip is at or near the vertical and/or horizontal center of the vial or another consistent location (e.g., 30%, 40%, 50%, 60% or 70% of the height of the vial) during each dispersing and/or agitating event in a series of withdrawing events. While the vertical center of the vial is typically appropriate for most series of withdrawing events, another position within the vial for each dispersing and/or agitating event may also be appropriate depending on the amount of solution and the type of particles within the vial.

In some embodiments, a vial rack configured to detachably associate with the shaker plate can be utilized to secure and stabilize the vials. Additionally, the vial rack can be utilized to align and/or secure the vials containing the solution with the pipettes of the shaker plate system for agitating the vial, dispersing solution into the vial and/or assay testing. In particular, the vial rack secures and stabilizes the vials during dispersing and/or agitating events, so that solution and particle agitation and/or position are consistent during the testing events (e.g., from assay to assay and/or operator to operator) using the same vials over multiple assays and/or using new samples in different vials.

Referring now to the figures, FIG. 1 is a simplified block diagram of an example computing device 100 of a system (e.g., those illustrated in FIGS. 2A-2B, described in further detail below). Computing device 100 can perform various acts and/or functions, such as those described in this disclosure. Computing device 100 can include various components, such as processor 102, data storage unit 104, communication interface 106, and/or user interface 108. These components can be connected to each other (or to another device, system, or other entity) via connection mechanism 110.

Processor 102 can include a general-purpose processor (e.g., a microprocessor) and/or a special-purpose processor (e.g., a digital signal processor (DSP)).

Data storage unit 104 can include one or more volatile, non-volatile, removable, and/or non-removable storage components, such as magnetic, optical, or flash storage, and/or can be integrated in whole or in part with processor 102. Further, data storage unit 104 can take the form of a non-transitory computer-readable storage medium, having stored thereon program instructions (e.g., compiled or non-compiled program logic and/or machine code) that, when executed by processor 102, cause computing device 100 to perform one or more acts and/or functions, such as those described in this disclosure. As such, computing device 100 can be configured to perform one or more acts and/or functions, such as those described in this disclosure. Such program instructions can define and/or be part of a discrete software application. In some instances, computing device 100 can execute program instructions in response to receiving an input, such as from communication interface 106 and/or user interface 108. Data storage unit 104 can also store other types of data, such as those types described in this disclosure.

Communication interface 106 can allow computing device 100 to connect to and/or communicate with another other entity according to one or more protocols. In one example, communication interface 106 can be a wired interface, such as an Ethernet interface or a high-definition serial-digital-interface (HD-SDI). In another example, communication interface 106 can be a wireless interface, such as a cellular or WI FI interface. In this disclosure, a connection can be a direct connection or an indirect connection, the latter being a connection that passes through and/or traverses one or more entities, such as such as a router, switcher, or other network device. Likewise, in this disclosure, a transmission can be a direct transmission or an indirect transmission.

User interface 108 can facilitate interaction between computing device 100 and a user of computing device 100, if applicable. As such, user interface 108 can include input components such as a keyboard, a keypad, a mouse, a touch sensitive panel, a microphone, a camera, and/or a movement sensor, all of which can be used to obtain data indicative of an environment of computing device 100, and/or output components such as a display device (which, for example, can be combined with a touch sensitive panel), a sound speaker, and/or a haptic feedback system. More generally, user interface 108 can include hardware and/or software components that facilitate interaction between computing device 100 and the user of the computing device 100.

Computing device 100 can take various forms, such as a workstation terminal, a desktop computer, a laptop, a tablet, a mobile phone, or a controller.

Figure 2:
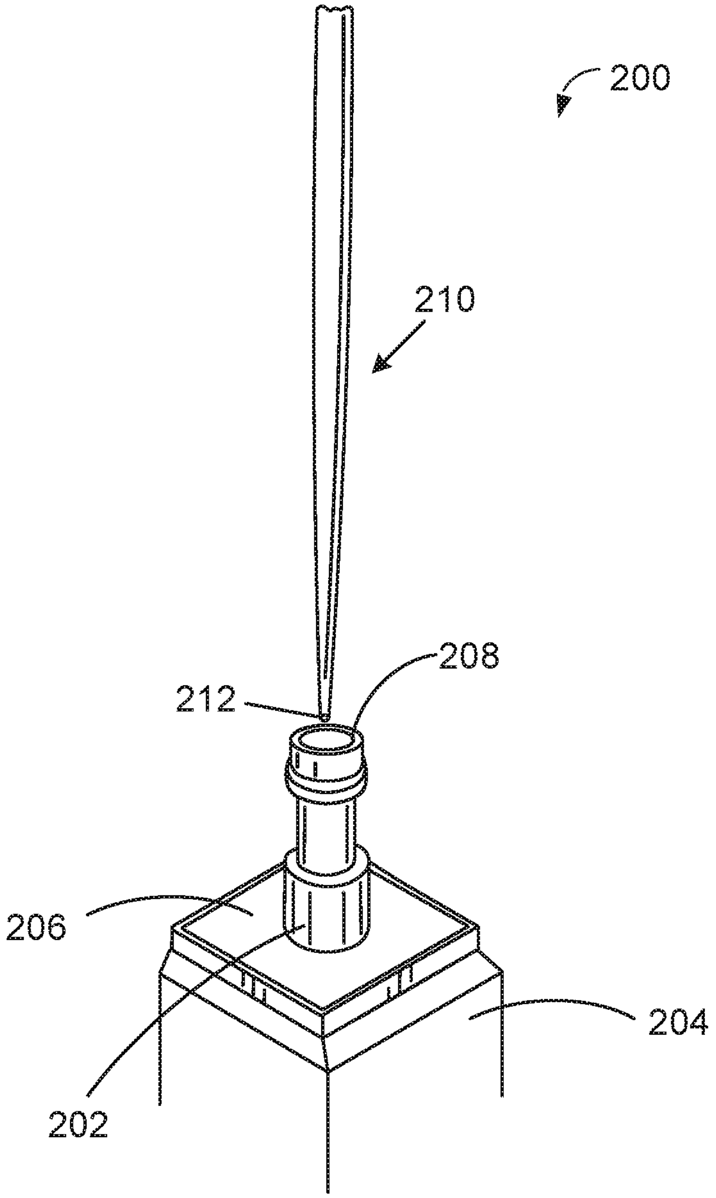
FIG. 2 illustrates a vial rack, pipette, and a shaker plate, according to an example embodiment.

Now referring to FIG. 2, a solution preparation system 200 is disclosed, which includes a vial rack 206, a shaker plate 204, a vial 208, and a pipette 210, according to an example embodiment. The vial rack 206 includes a base coupled to one vial receptacle 202, suitable for holding vial 208. Although illustrated in FIG. 2 as holding one vial 208, vial rack 206 may be configured to hold more than one vial, for example, by implementing more than one vial receptacle 202, over a number of configurations. For example, vial racks 206 according to the present disclosure can include any number of vial receptacles (thirty two vial receptacles), in any number of configurations (four rows of eight vial receptacles). In practice, the alignment of vial receptacles 202 may be desirable to integrate with specific instrumentation (e.g., a specific reader and/or pipette, including a Hamilton® Genomic STARlet, which includes 8 pipettes).

In some examples, the vial receptacle 202 is configured to hold a variety of vials, some or all of which may meet Society for Biomolecular Screening ("SBS") standards or other industry standard for laboratory equipment. In the embodiment shown in FIG. 2, the vial receptacle 202 is aligned to position the vial 208 such that an SBS standard pipettes (for example, pipette 210) can be inserted in and dispense buffer solution into each vial. Namely, the vial receptacle 202 may be designed to space vials similarly to standard SBS pipette tips, such as the Hamilton® SPAN8-channel pipetting mechanism. Additionally, although various components of the systems and/or methods described herein may refer to SBS-compliment components, they are described for the purposes of illustrating example embodiments and other, addition The vial rack 206 may also be detachably associated with the shaker plate 204 by way of a fastening mechanism, such as a screw or other threaded connection in a manner that is not destructive to the vial rack 206, the vial receptacle 202, the shaker plate 204, the pipette 210, and/or other components of the illustrated devices. In some examples, the dimensions of the surface of the vial rack 206 are the same or substantially similar with the shaker plate 204.

In examples, the shaker plate 204 and pipette 210 are part of a shaker plate system which includes a computing device, such as computing device 100. As described above, a computing device 100 can be implemented as a controller, and a user of the controller can use the controller to control a shaker plate 204 and pipette 210. The shaker plate 204 and pipette 210 communicably coupled with a controller, such as computing device 100, and may communicate with the controller by way of a wired connection, a wireless connection, or a combination thereof.

In examples, the controller can execute a program that causes the shaker plate 204 and pipette 210 to perform a series of agitating and/or dispensing events by way of a non-transitory computer-readable medium having stored program instructions. These program instructions include, for example, shaker plate 204 mixing speed (e.g., rotational velocity), mixing pattern, and dispensing rate and/or amount of buffer solution dispersed into the vial 208. Certain mixing speeds, mixing patterns, and pipette placement may more effectively agitate the solution to produce more accurate and consistent particle counts than other mixing speeds, patterns, and pipette tip positions.

For example, the controller program instructions can include moving the shaker plate 204 at a first predetermined speed while the vial rack 206 is coupled to the shaker plate 204 and includes at least one vial containing a solution in a vial receptacle 202. This first predetermined speed corresponds to a first agitating and dispersing event of the buffer solution in the vial. Further, in practice, shaking the shaker plate 204 at this first predetermined speed while dispersing, into the vial, during the agitating, a first volume of buffer solution at a first predetermined dispensing rate suspends a plurality of particles (e.g., paramagnetic beads and/or polystyrene particles) within the solution.

In some examples, the controller can cause the shaker plate 204 to shake in orbital pattern while dispersing the buffer solution, consequently agitating the vials 208 and solution in the orbital pattern. In other examples, the controller can cause the shaker plate 204 to shake in a linear pattern, consequently agitating the vials 208 and solution in the linear pattern.

Further, in some examples, the program instructions can include moving the shaker plate 204 at various mixing speeds, over a variety of mixing patterns (e.g., orbital mixing patterns, linear mixing patterns, etc.). Furthermore, the program instructions can include moving the shaker plate 204 and agitating the vials 208 (all while dispersing the buffer solution) within a predetermined range of mixing speeds. For example, in one embodiment, the program instructions may include moving the shaker plate 204 at a mixing speed between about 400 revolutions per minute (rpm) and about 600 rpm. As described in more detail with respect to FIGS. 3A-4C, this mixing speed range is desirable to suspend the particles without forming bubbles in the solutions, which could negatively impact the assay read. Regarding these embodiments, one or more operators may also manually attach the vial rack 206 to shaker plate 204 and then set a mixing speed and/or mixing pattern on the shaker plate 204 prior to the pipette 210 being inserted in vial 208.

In some embodiments, the controller causes the pipette 210 to be positioned such that the corresponding pipette tip is at a first predetermined depth within the corresponding vial 208 during the agitation and dispersing events. This predetermined depth may correspond to characteristics of the vial 208 and/or a substance contained therein. For example, the predetermined depth may be at or near the vertical center of the vial which may more effectively agitate and homogenize the particles in the vial as the buffer solution is dispersed into the vial to produce more consistent particle counts for the particles in the solution (e.g., paramagnetic bead counts).

In embodiments, the controller may cause the pipette 210, during the agitating to dispense a predetermined volume of buffer solution, perhaps at a predetermined dispensing rate. This predetermined volume of solution and/or dispensing rate may also influence the pipette 210 position for subsequent agitation and dispersing events. Furthermore, the program instructions can include dispersing a predetermined volume of the buffer solution within a predetermined range of dispensing rates. For example, in one embodiment, the program instructions may include dispersing between 180 microliters of buffer solution and 220 microliters of buffer solution. In another example embodiment, the program instructions may include dispensing the buffer solution between about 270 microliters of buffer solution per second and 330 microliters of buffer solution per second. As described in more detail with respect to FIGS. 3A-4D, this amount and/or dispensing rate of buffer solution is desirable to suspend the particles without forming bubbles in the solutions and/or damage the assembled particles, which could negatively impact the assay read. Regarding these embodiments, one or more operators may also manually attach the vial rack 206 to shaker plate 204 and then use pipette 210 to dispense a predetermined amount of buffer solution at a predetermined dispensing rate into vial 208 during an agitating event.

This sequence of agitation and dispersing the buffer solution may be repeated a number of times. For instance, in some examples, during a second agitating event, the controller may cause the shaker plate 204 to move at a second predetermined speed while the vial rack 206 is coupled to the shaker plate 204 and includes at least one vial 208 containing a solution in a vial receptacle 202. Additionally, during this second agitating event, the end of the pipette tip may be positioned at a second predetermined depth within the vial 208. In some examples, the first predetermined depth is the same as the second predetermined depth. Alternately, in some examples, this second predetermined depth is different from the first predetermined depth. Namely, each predetermined depth corresponds to substances in the vial 208 during a dispensing event.

This process may be repeated for subsequent dispensing events. Namely, the controller may cause the shaker plate 204 to agitate the vials 208 and the pipette 210 to dispense a predetermined volume of buffer solution at a predetermined dispensing rate in the vial repeatedly. Each agitation and/or dispensing event in a series may be performed at the same mixing speed, mixing pattern, the end of the pipette tip depth, and/or using the same volume of buffer solution. Alternatively, these various settings may change between each agitation and/or dispensing event in a series. In some examples, the pipette may be used to agitate the assembled particle and buffer solution mixture by aspirating the solution and/or stirring the solution, among other possibilities. In other examples, agitation can also involve rapidly withdrawing and dispensing the assembled particle and buffer solution mixture.

Additionally, in some example embodiments, the one or more components of the shaker plate system may provide feedback to a user/operator. For example, the plate shaker system may provide an alert signal (e.g., via a user interface of the controller and/or the shaker plate) to provide an indication to the user that the mixing speeds are outside of a predetermined range (e.g., if the mixing speed of the shaker plate 204 is below about 400 rpm or above about 600 rpm).

In some example embodiments, the shaker plate 204 can be stopped and the vial can be transported to a reader to conduct the assay testing. In example embodiments, the reader may detect, shortly after the agitating and the dispersing events, an assay read signal corresponding to at least one of the particles of the plurality of particles. In some example embodiments, this detection may occur within a predetermined time period after completing the agitating and the dispersing (e.g., the vial is placed in the reader and the assay testing begins approximately one minute after the conclusion of the agitating and the dispersing events). In these embodiments, by starting the assay read shortly after the conclusion of the agitating and the dispersing events can result in further dispersion of the particles before conducting the assay to provide a more accurate particle count.

Figure 3A:
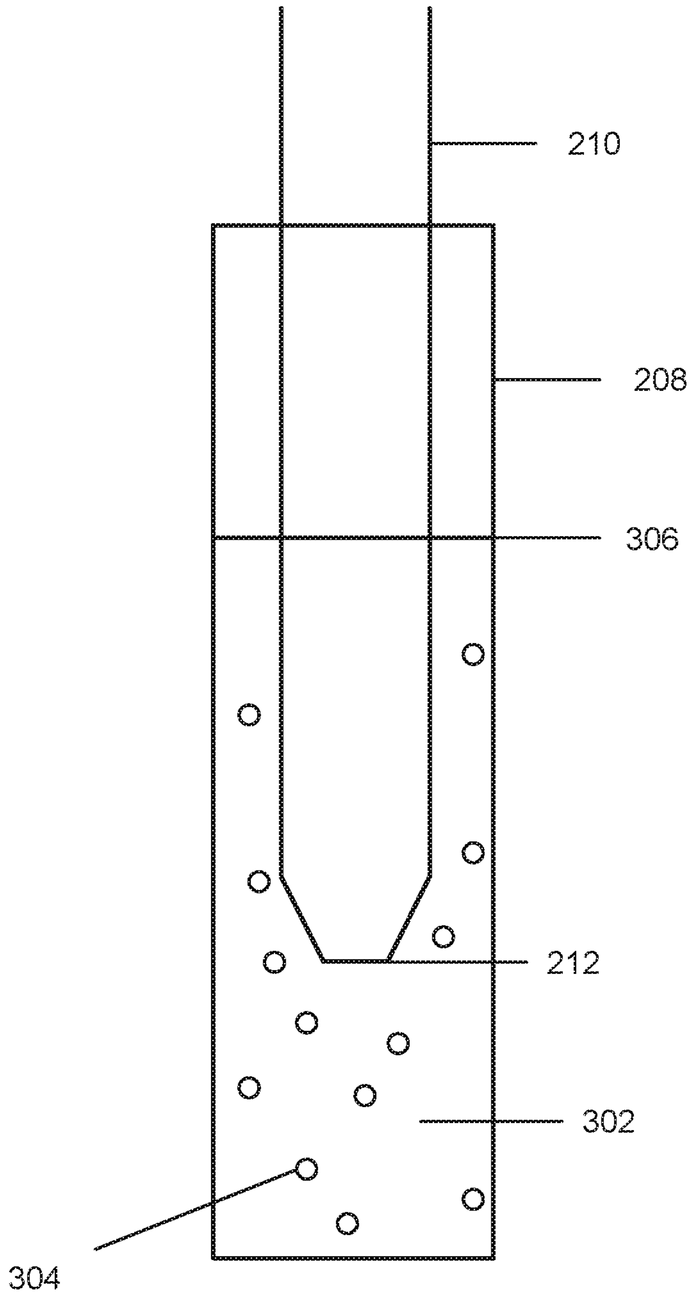
FIG. 3A illustrates a vial and an end of a pipette tip of the pipette of FIG. 2, according to an example embodiment.
Figure 3B:
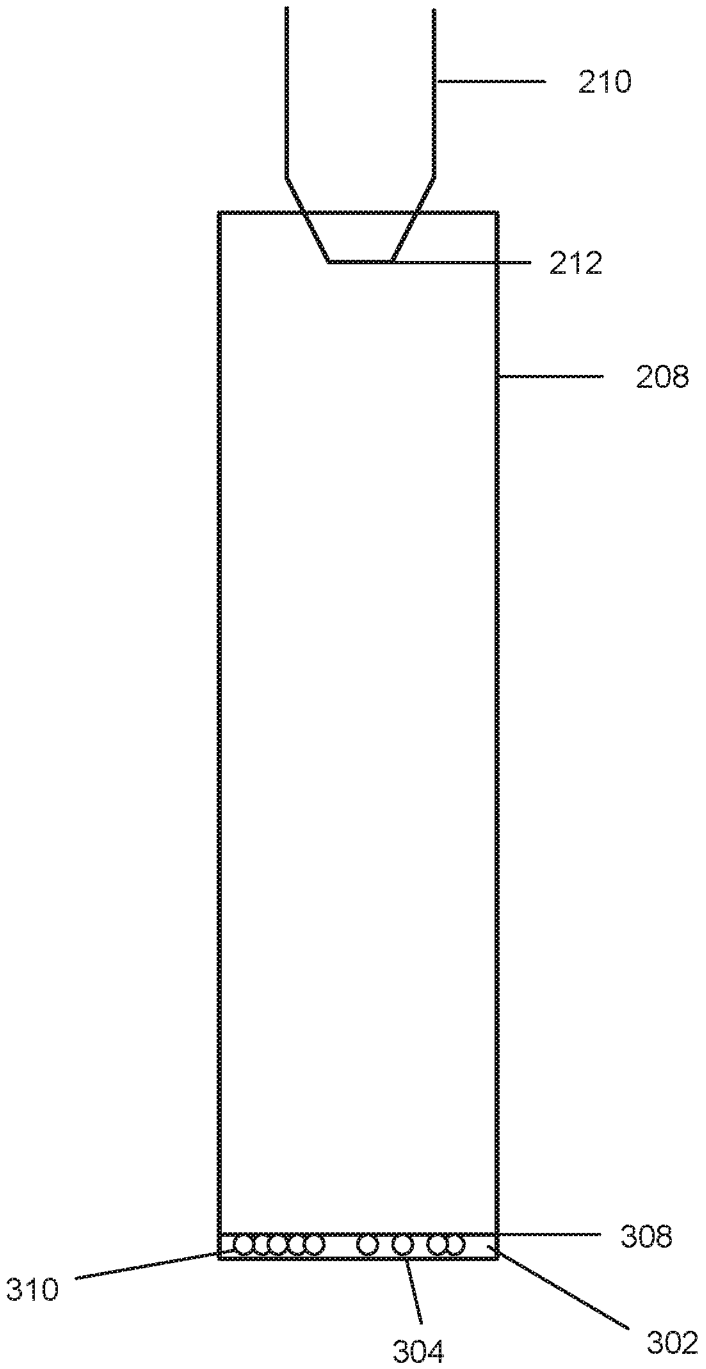
FIG. 3B illustrates the vial and the end of the pipette tip of the pipette of FIG. 3A, according to an example embodiment.
Figure 3C:
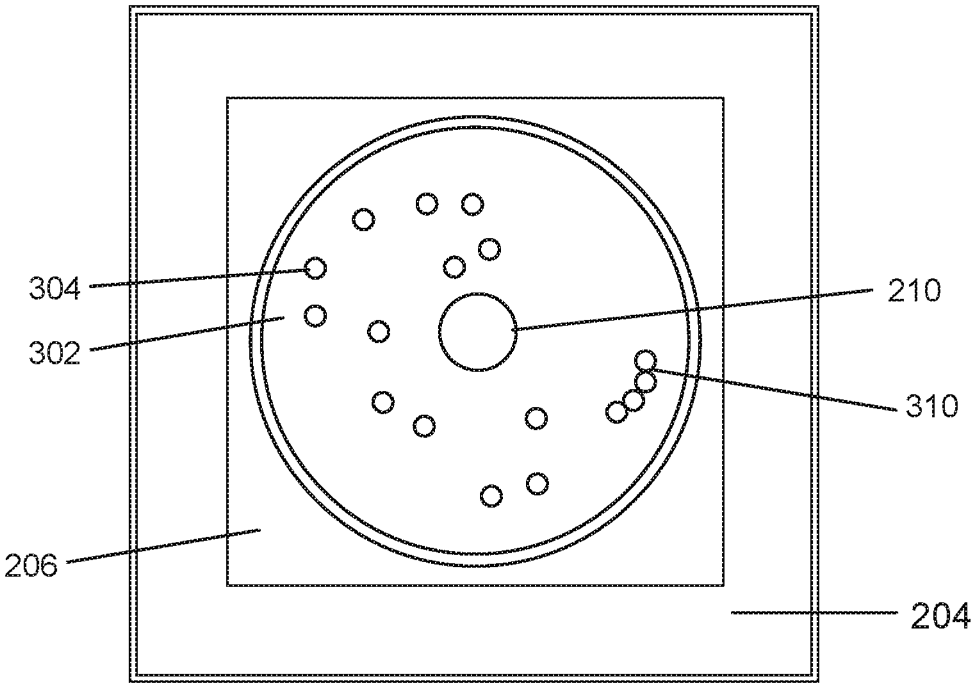
FIG. 3C illustrates the vial and the end of the pipette tip of the pipette of FIG. 3B and a shaker plate from a top view perspective, according to an example embodiment.
Figure 3D:
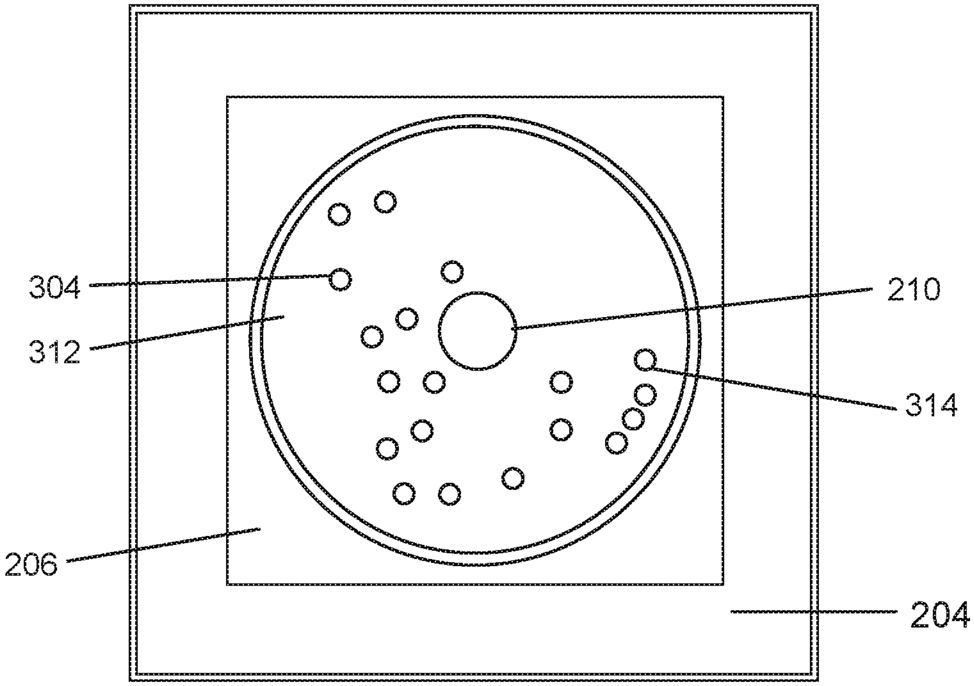
FIG. 3D illustrates the vial, the end of the pipette tip of the pipette, and the shaker plate of FIG. 3C, according to an example embodiment.

Now referring to FIGS. 3A-3C, a pipette 210 and a vial 208 according to example embodiments and configurations. Namely, FIG. 3A illustrates an end of the pipette tip 212 within the vial 208, with the end of the pipette tip at or near the center or middle of the horizontal cross section of the vial (the "horizontal center") before solution that is used to wash the assembled particles ("washing solution) prior to the assay. FIG. 3B illustrates the end of the pipette tip 212 at a second predetermined depth within the vial 208 after washing solution has been withdrawn, but before the buffer solution has been dispensed in vial 208. FIG. 3C illustrates a top down view of the vial 208 and pipette 210 after the washing solution has been withdrawn, but before the buffer solution has been dispensed in vial 208. FIG. 3D illustrates a top down view of the vial 208 and pipette 210 after the agitating event has occurred and the buffer solution has been dispensed in vial 208.

In example embodiments, in FIGS. 3A-3D, the vial 208 includes particles 304. These particles may be utilized during one or more assay procedures, including, for example, to identify a particular type and/or subset of components within a sample, such as antigens, antibodies, proteins, or the like.

In example embodiments, in FIGS. 3A-3C, the vial 208 contains a solution 302 (e.g., a washing solution). In FIG. 3A, the vial 208 contains a solution 302 at a first height 306 (e.g., a washing solution), which includes particles 304.

Turning to FIG. 3B, in FIG. 3B, solution 302 has been removed from the vial 208, such that a very small amount (if any) of solution 302 remains at a second height 308 (i.e., all (or approximately all) of the washing solution has been removed). As illustrated in FIG. 3B, particles 304 remain in vial 208, but some of the particles 304 have bound (or clumped) together as bound particles 310. As noted above, the presence of these bound particles 310 may create unwanted structures and/or non-homogenized dispersion in the solution to be used in the assay, which may lead to inconsistent or inaccurate results from the assay.

As discussed in further detail above, these bound particles 310 may result from the particles 304 being left in the bottom of vial 208 after the solution 302 is removed. Additionally or alternatively, bound particles 310 may result from particles 304 having magnetic or paramagnetic properties. Additionally or alternatively, bound particles 310 may result from particles 304 having magnetic or paramagnetic properties and a magnet being used to secure the particles 304 in the vial 208 (e.g., during washing). Other examples are possible.

Turning to FIG. 3C, in FIG. 3C, a top down view of the components of FIG. 3B, which includes, particles 304, bound particles 310, and solution 302 (if any remains), as well as vial rack 206, shaker plate 204, and pipette 210, are illustrated.

In FIG. 3D, the components of FIG. 3C are illustrated, as well as buffer solution 312 and unbound particles 314. In FIG. 3D, in an example embodiment, pipette 210 has dispersed between 180 microliters and 220 microliters of buffer solution 312 at dispensing rate of between about 270 microliters and 330 microliters of buffer solution per second into vial 208. Additionally, in FIG. 3D, in an example embodiment, shaker plate 204 has moved shaker plate 204 in an orbital pattern while dispersing the buffer solution, consequently agitating the vials 208 and solution 312 and particles 304 in the orbital pattern. In some examples, moving the vial in the orbital pattern comprises moving a center of the vial up to 3 millimeters from a horizontal center. In an example embodiment, the shaker plate 204 has moved the vial rack 206 (and thereby the vial and solution therein) at a mixing speed between about 400 revolutions per minute (rpm) and about 600 rpm. As further illustrated in FIG. 3D, this protocol results in the bound particles 310 of FIG. 3C becoming the unbound particles 314 of FIG. 4D, which results in improved homogenization the solution and particles of FIG. 3D. In a further aspect, this improved homogenization also results in improved assays using the solution and particles of FIG. 3D (compared to those illustrated in FIGS. 3A-3C).

As described above, a controller is configured to control the agitating and/or dispensing events of FIGS. 3A-3D, as well as position the end of the pipette tip 212. Although particular components and agitating and dispensing configurations are shown in FIGS. 3A-3D, it should be understood that many other particular components and agitating and dispensing configurations can be achieved based on various configurations and examples. It should also be noted that although round particles are illustrated in FIGS. 3A-3D, different shapes, amounts, and/or types of particles may be used.

FIGS. 4A-4D show the example embodiment of FIGS. 3A-3D, except the solution 402 includes paramagnetic beads 404. In some example embodiments, each of the paramagnetic beads 404 includes a unique bar code. In another example, each of the paramagnetic beads 404 includes two or more unique bar codes and/or binding members that are attached to paramagnetic beads 404. Additionally, these particles, binding members, and/or combinations of the two, may exhibit one or more unique identifying features.

In yet another example, a subset of the paramagnetic beads 404 may include one unique bar code and the remaining paramagnetic beads 404 may include two or more unique bar codes. In practice, each of these bar codes may correspond to particular information about the paramagnetic bead, the solution, and/or one or more additional parameters and/or unique identifying features (including those used in an assay). For example, these unique bar codes may be utilized during one or more assay procedures, including, for example, to identify a particular type and/or subset of paramagnetic beads within the solution that are associated with a specific assay.

In example embodiments, in FIGS. 4A-4D, the vial 208 includes paramagnetic beads 404. These particles may be utilized during one or more assay procedures, including, for example, to identify a particular type and/or subset of particles within the solution.

Figure 4A:
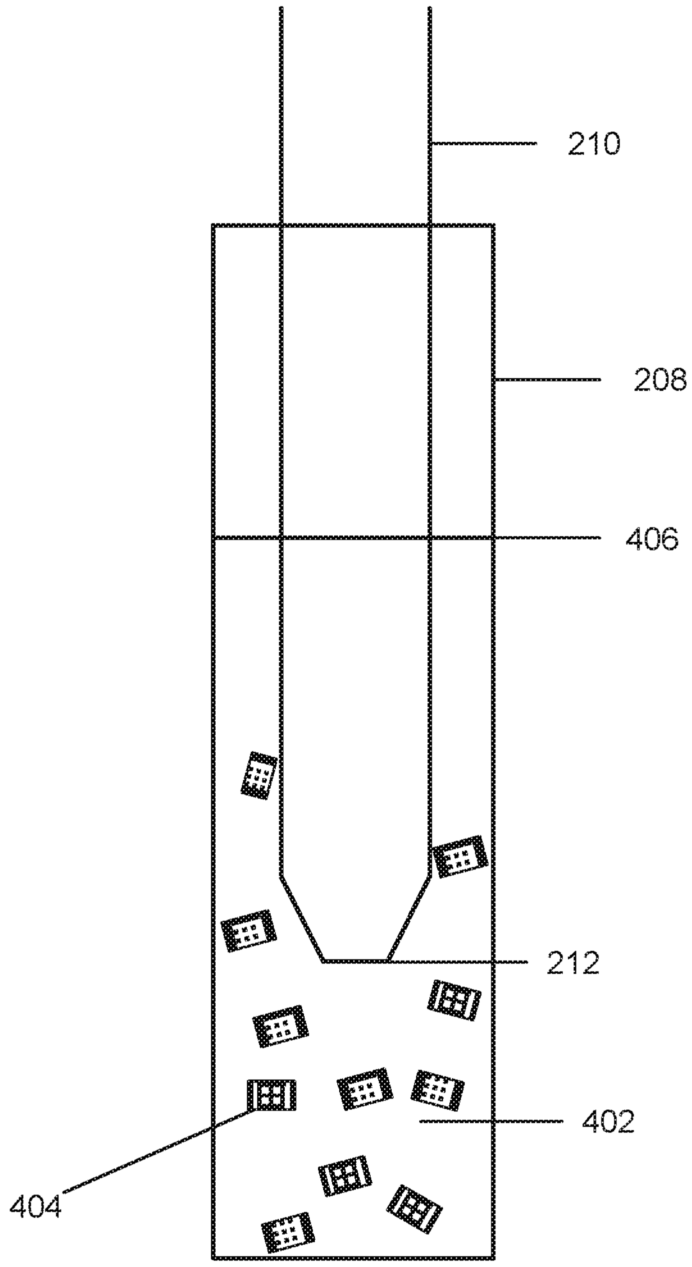
FIG. 4A illustrates another vial and an end of a pipette tip of the pipette of FIG. 2, according to an example embodiment.
Figure 4B:
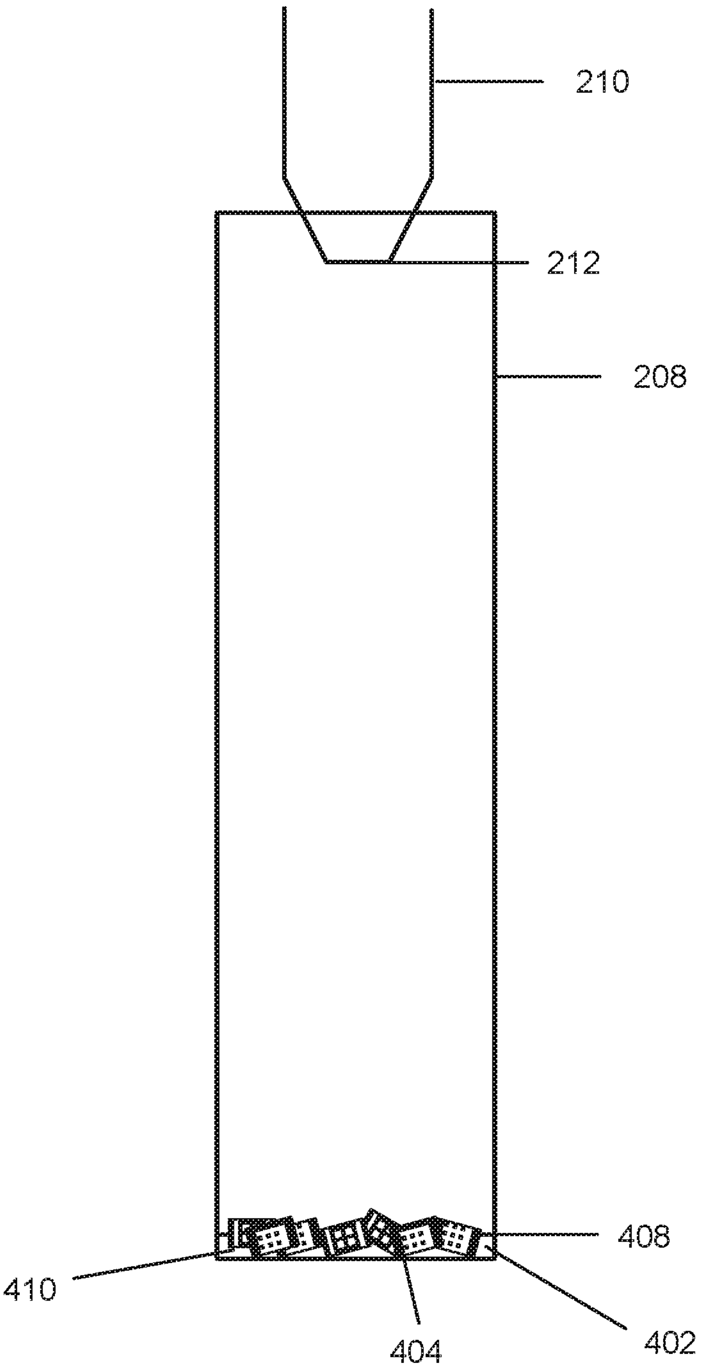
FIG. 4B illustrates the vial and the end of the pipette tip of the pipette of FIG. 3A, according to an example embodiment.
Figure 4C:
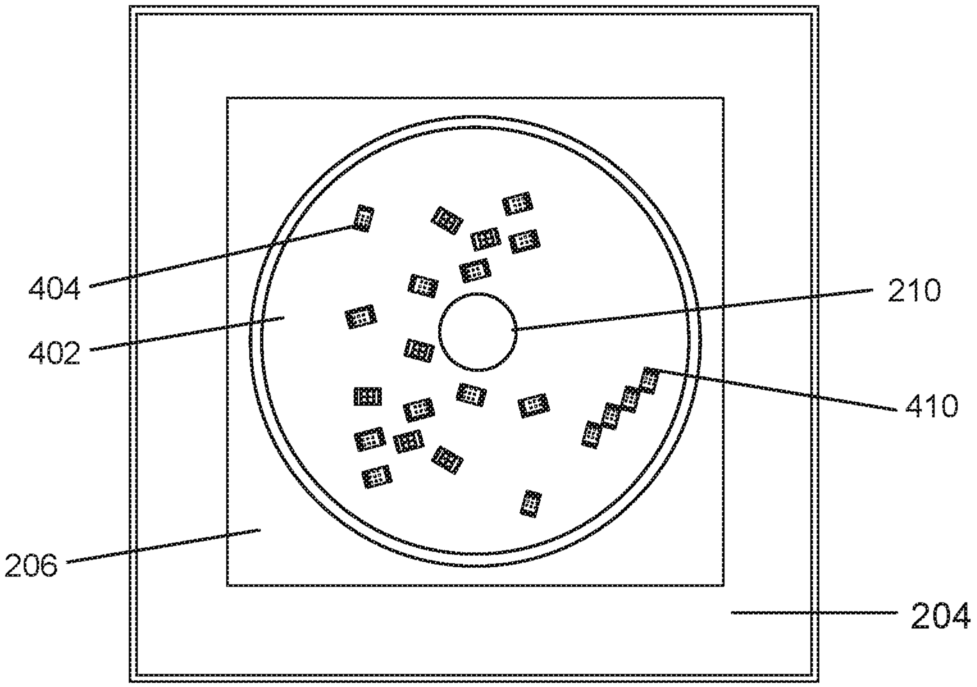
FIG. 4C illustrates the vial and the end of the pipette tip of the pipette of FIG. 4B and a shaker plate from a top view perspective, according to an example embodiment.

In example embodiments, in FIGS. 4A-4C, the vial 208 contains a solution 402 (e.g., a washing solution). In FIG. 4A, the vial 208 contains a solution 402 at a first height 406 (e.g., a washing solution), which includes paramagnetic beads 404.

Turning to FIG. 4B, in FIG. 4B, solution 402 has been removed from the vial 208, such that a very small amount (if any) of solution 402 remains at a second height 408 (i.e., all (or approximately all) of the washing solution has been removed). As illustrated in FIG. 4B, paramagnetic beads 404 remain in vial 208, but some of the paramagnetic beads 404 have bound (or clumped) together as bound particles 410. As noted above, the presence of these bound particles 410 may create unwanted structures and/or non-homogenized dispersion in the solution to be used in the assay, which may lead to inconsistent or inaccurate results from the assay.

As discussed in further detail above, these bound particles 410 may result from the paramagnetic beads 404 being left in the bottom of vial 208 after the solution 402 is removed. Additionally or alternatively, bound particles 410 may result from paramagnetic beads 404 from a magnet being used to secure the paramagnetic beads 404 in the vial 208 (e.g., during washing). Other examples are possible.

Turning to FIG. 4C, in FIG. 4C, a top down view of the components of FIG. 4B, which includes, paramagnetic beads 404, bound particles 410, and solution 402 (if any remains), as well as vial rack 206, shaker plate 204, and pipette 210, are illustrated.

Figure 4D:
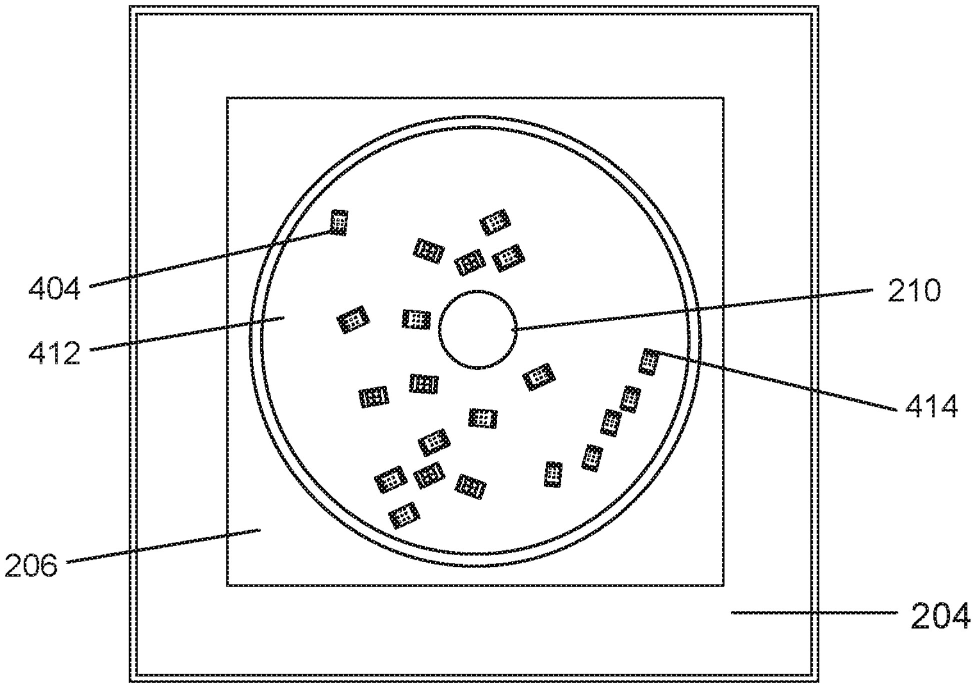
FIG. 4D illustrates the vial, the end of the pipette tip of the pipette, and the shaker plate of FIG. 4C, according to an example embodiment.

Turning to FIG. 4D, in FIG. 4D, the components of FIG. 4C are illustrated, as well as buffer solution 412 and unbound particles 414. In FIG. 4D, in an example embodiment, pipette 210 has dispersed between 180 microliters and 220 microliters of buffer solution 412 at dispensing rate of between about 270 microliters and 330 microliters of buffer solution per second into vial 208. Additionally, in FIG. 4D, in an example embodiment, shaker plate 204 has moved shaker plate 204 in an orbital pattern while dispersing the buffer solution, consequently agitating the vials 208 and solution 412 and paramagnetic beads 404 in the orbital pattern. In an example embodiment, the shaker plate 204 has moved the vial rack 206 (and thereby the vial and solution therein) at a mixing speed between about 400 revolutions per minute (rpm) and about 600 rpm. In some examples, moving the vial in the orbital pattern comprises moving a center of the vial up to 3 millimeters from a horizontal center. As further illustrated in FIG. 4D, this protocol results in the bound particles 410 of FIG. 4C becoming the unbound particles 414 of FIG. 4D, which results in improved homogenization the solution and particles of FIG. 4D. In a further aspect, this improved homogenization also results in improved assays using the solution and particles of FIG. 4D (compared to those illustrated in FIGS. 4A-4C).

As described above, a controller is configured to control the agitating and/or dispensing events of FIGS. 4A-4D, as well as position the end of the pipette tip 212. Although particular components and agitating and dispensing configurations are shown in FIGS. 4A-4D, it should be understood that many other particular components and agitating and dispensing configurations can be achieved based on various configurations and examples. It should also be noted that although round particles are illustrated in FIGS. 4A-3D, different shapes, amounts, and/or types of particles may be used.

In a further aspect, to evaluate the efficacy of homogenizing a solution containing a plurality of particles one or more of the example embodiments described above, one or more devices, systems, or methods may be employed.

For example, if particles in a prepared solution are not even distributed throughout the solution prior to a withdrawing event (e.g. because of clumping, binding/settling on the bottom or sides of the vessel in which the solution containing the particles is prepared, etc.), the particles may remain in the vessel as solution is pipetted out of the vessel. To help measure the dispersion and consistency of particles in a solution, an aliquot of the prepared solution may be transferred onto a surface (e.g., a Petri dish, a well, or the like) and a composite image of the transferred aliquot of solution may be generated. In examples, this composite image may contain a plurality of images of the transferred aliquot of solution and based on one or more attributes of this generated composite image, one or more parameters may be determined for the transferred aliquot of solution. Other examples are possible.

For example, the composite image may also be used to identify one or more characteristics of the individual particles in the transferred aliquot of solution. For example, if the particles include paramagnetic beads that include one or more unique bar codes, the composite image may be used to identify one or more unique bar codes in the image corresponding to the individual particles in the transferred aliquot of solution. In example embodiments, the one or more unique bar codes identified in the composite image can also be used to determine an assay result. In example embodiments, the one or more unique bar codes identified in the composite image can also be compared to an assay result generated from another source (e.g., a reader) and/or used to determine the accuracy of the results from another source (e.g., by comparing the assay results from the reader to those determined from the composite image).

In FIGS. 5A-5D, a sample of solution 502 containing particles is illustrated according to an example embodiment. These particles may be utilized during one or more assay procedures, including, for example, to identify a particular type and/or subset of components within a sample. In the example embodiment illustrated in FIGS. 5A-5D, the solution 502 includes paramagnetic beads 504. In some example embodiments, each of the paramagnetic beads 504 includes a unique bar code. In another example, each of the paramagnetic beads 504 includes two or more unique bar codes.

In yet another example, a subset of the paramagnetic beads 504 may include one unique bar code and the remaining paramagnetic beads 504 may include two or more unique bar codes. In practice, each of these bar codes may correspond to particular information about the paramagnetic bead, the solution, and/or one or more additional parameters (including those used in an assay). For example, these unique bar codes may be utilized during one or more assay procedures to identify a particular type and/or subset of paramagnetic beads within the solution.

It should also be noted that although the particles illustrated in FIGS. 5A-5D involve paramagnetic beads, different shapes, amounts, and/or types of particles may be used.

It should also be noted that one or more concepts illustrated in FIGS. 5A-5D may be accomplished using a computing device, such as computing device 100. As described above, a computing device 100 can be implemented as a controller, and a user of the controller can use the controller to control the capturing of one or more images of the solution, as well as process the plurality of images to generate and/or annotate a composite image of the plurality of images.

In examples, the controller can execute a program that causes the controller and/or components operating therewith (e.g., a camera) to perform a series of actions by way of a non-transitory computer-readable medium having stored program instructions.

Figure 5A:
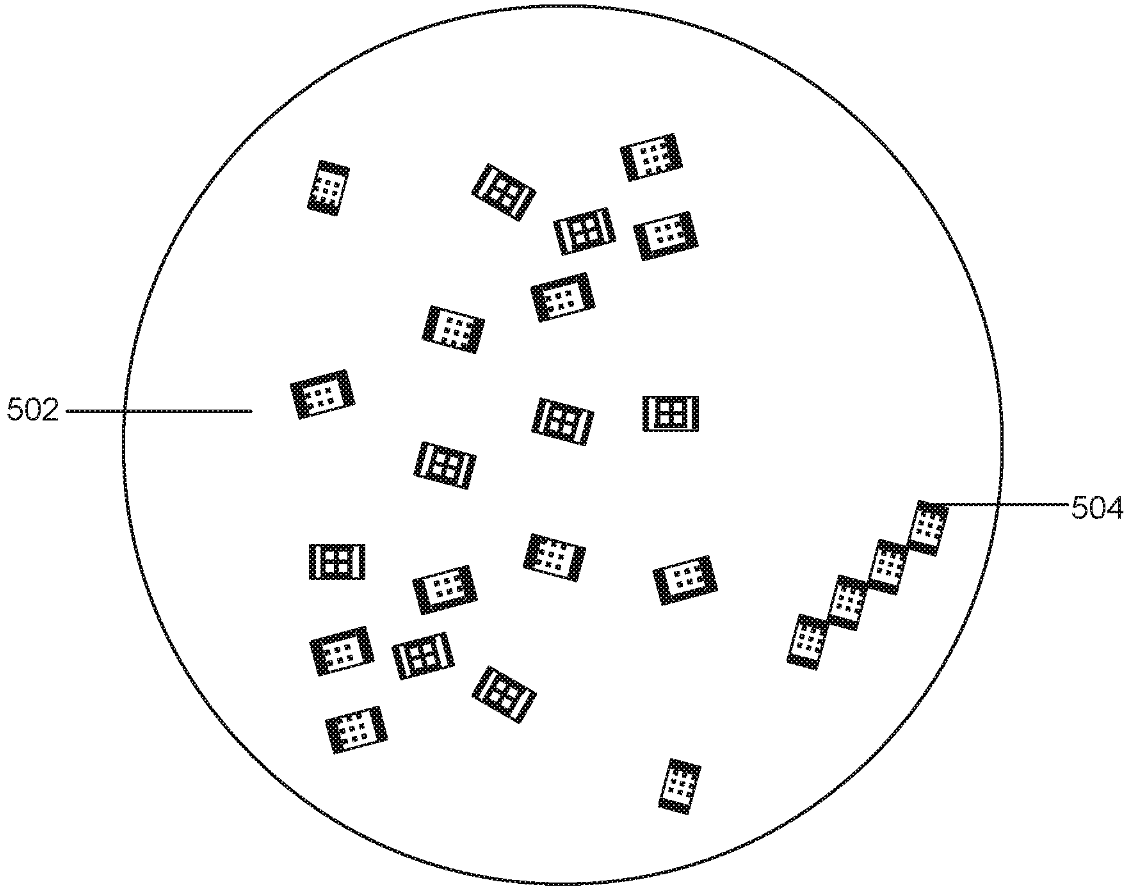
FIG. 5A illustrates a sample of prepared solution containing particles according to an example embodiment.
Figure 5B:
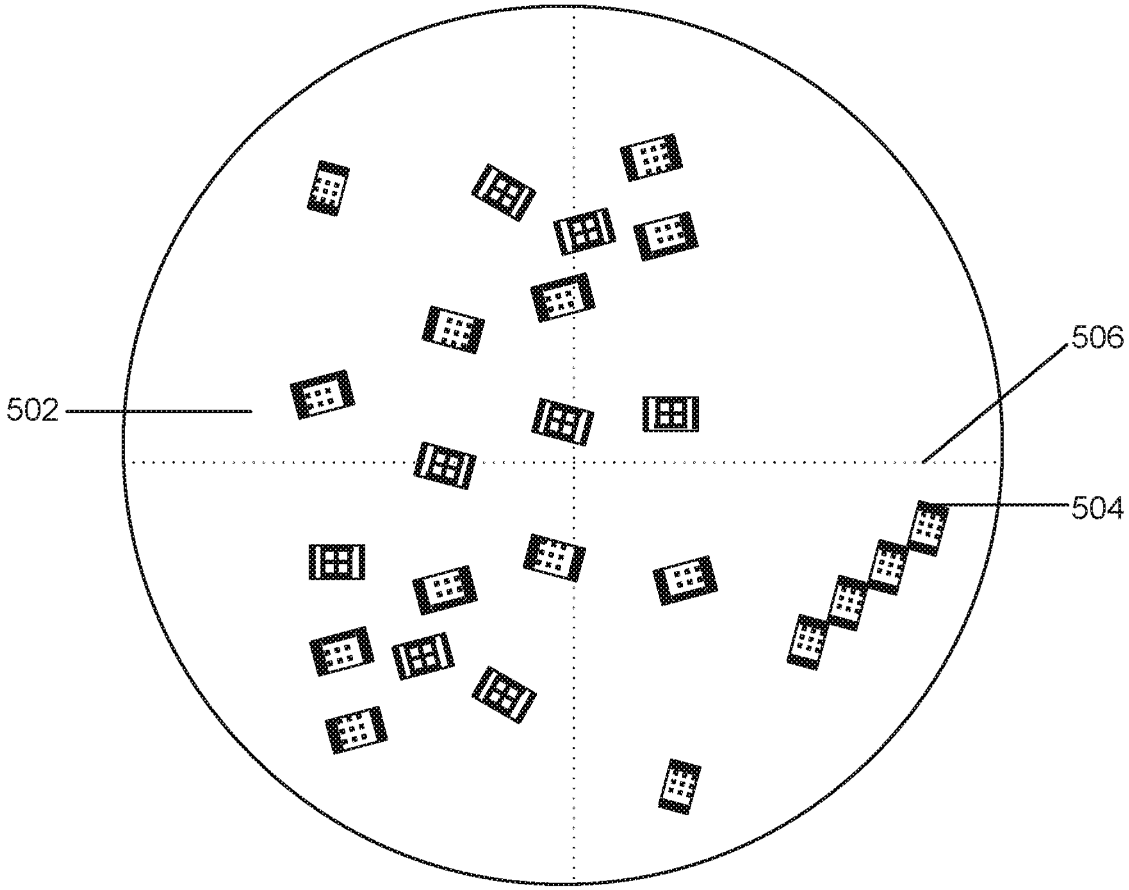
FIG. 5B illustrates an image of the sample of prepared solution containing particles of FIG. 5A, according to an example embodiment.

In FIG. 5A, a sample of the prepared solution transferred onto a surface is illustrated, wherein the prepared solution comprises the first volume of buffer solution and the plurality of particles. Turning to FIG. 5B, an example segmentation 506 of the surface is illustrated, in which the surface has been divided into four quadrants for imaging. In example embodiments, segmentation of the illustrated surface may include different sizes, shapes, numbers, and configurations of segments to be imaged for the transferred solution, depending on one or more characteristics of the sample (e.g., one or more bar codes of the particles, particle size, particle concentration, etc.) and/or the image analysis to be undertaken. Once the segmentation 506, one or more images may be captured for each of the one or more segments and used for further processing.

Figure 5C:
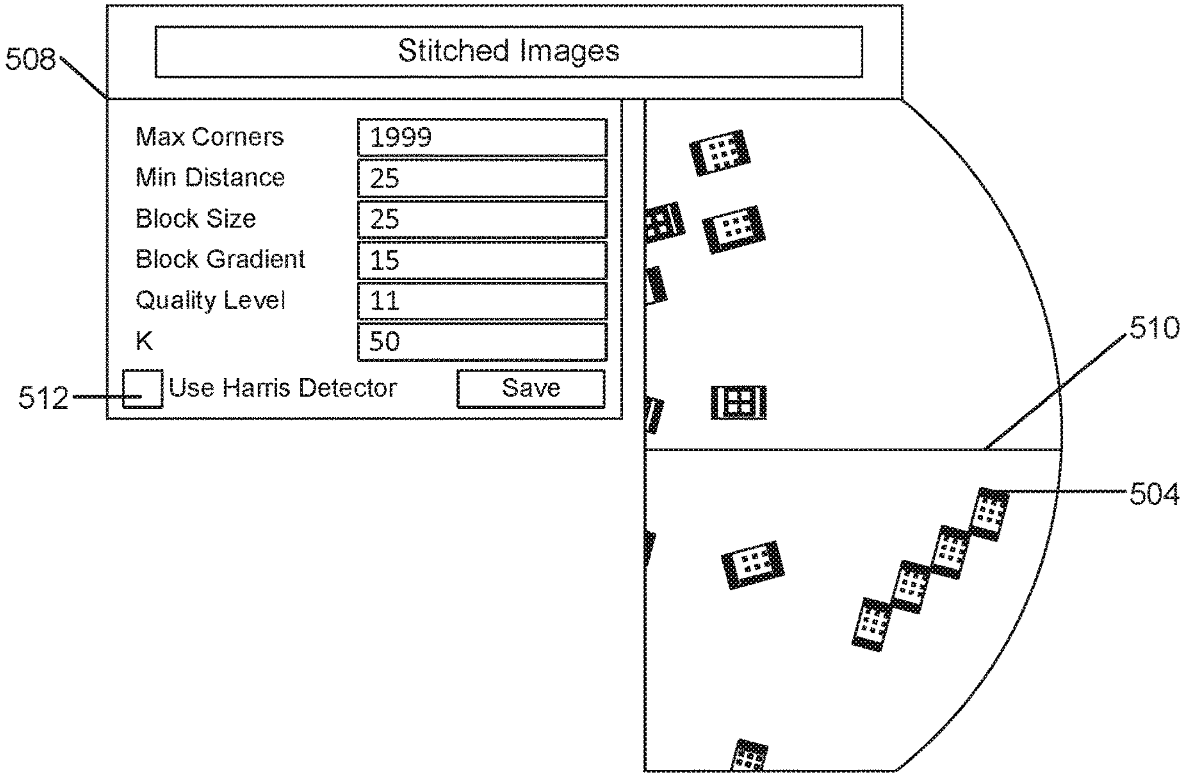
FIG. 5C illustrates a composite image of the sample of solution containing particles of FIGS. 5A and 5B and an associated graphical user interface, according to an example embodiment.

Turning to FIG. 5C, an example composite image 510 of a plurality of images captured across one or more segments of the solution is illustrated. In example embodiments, composite image 510 may be generated by stitching the plurality of images of the transferred aliquot of solution into the composite image of the transferred aliquot of solution illustrated in FIG. 5C. In example embodiments, a controller may stich together the plurality of images of the transferred aliquot of solution that contain particles and remove any images that do not contain particles. In example embodiments, the controller may determine which images in the plurality of images of the transferred aliquot of solution that contain particles by performing one or more of a pixel density and/or gradient analysis of the individual images captured by the controller. In some example embodiments, the particles in the solution (e.g., paramagnetic beads 504) may present a different contrast and/or pixel density compared the solution in which the particles are disposed (shown in FIGS. 5A-5D as the dark, black portions of paramagnetic beads 404 compared to the light, white portions of the surround solution 502). Prior to stitching, as illustrated in the example graphical user interface 508 of FIG. 5C, a user may set one or more parameters for the stitching protocol, including which images should be stitched together, as well as one or more attributes of the stitched image and/or stitching protocol (shown in FIG. 5C as "Max Corners," "Min Distance," "Block Size," "Block Gradient," "K"). Other examples are possible.

Once composite image 510 has been generated, further analysis may be undertaken on the composite image 510 to determine one or more parameters of the transferred aliquot of solution and/or the particles contained therein. In example embodiments, as shown in the example graphical user interface 508 of FIG. 5C, a user may want to determine one or more attributes of the solution, including a count of the particles in the transferred sample. To do so, the user may select to use one or more programs executing a variety of automated protocols, including one or more edge detection protocols. In an example embodiment, as illustrated in FIG. 5C, a user may select to use a Harris corner detection algorithm (shown in FIG. 5C as "Use Harris Detector" prompt 512) to perform this edge detection for the particles in the solution and thereby generate a count of the particles in the solution. In example embodiments, the controller may use one or more algorithms (including Harris corner detection) and/or protocols to detect an edge of a particle in the composite image, based at least in part on detecting an edge of the particle in the composite image, determining a presence of at least one particle in the composite image. Other examples, including the use of other image processing and/or machine learning and artificial intelligence algorithms, are possible. For example, one or more machine learning models may comprise a deep learning model and/or image pixel and/or gradient analysis models.

Figure 5D:
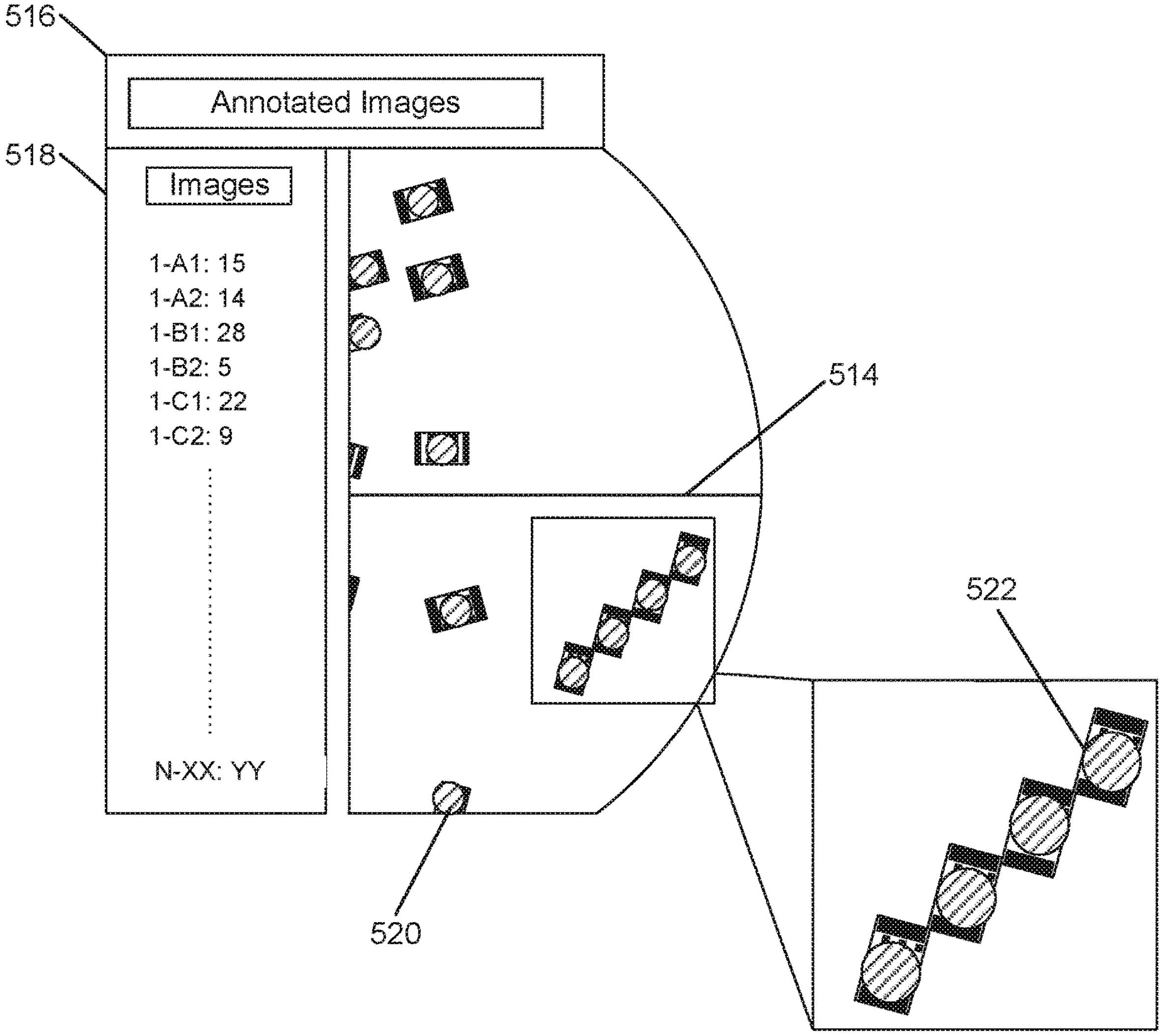
FIG. 5D illustrates an annotated version of the composite image of FIG. 5D and an associated graphical user interface, according to an example embodiment.

Turning to FIG. 5D, an example annotated image 514 of a plurality of particles detected in the composite image 510 is illustrated. In example embodiments, the controller may determine the count of the particles in solution by identifying the particles in the solution and generate annotated image 514 by utilizing one or more edge detection protocols (including the Harris corner detection algorithm). In example embodiments, the controller may perform this edge detection for the particles in the solution, generate a count of the particles in the solution, and present annotated images of the particles identified and/or counted in the annotated image 514. For example, as shown in example graphical user interface 516 of FIG. 5D, in example embodiments, the controller may present the user with an image accounting 518 of all of the images that were stitched together and/or annotated, as well as one or more attributes of the stitched image and/or stitching protocol (e.g., how many particles were identified in each image and/or segment of sample and/or corresponding images). Other examples are possible.

Once annotated image 514 has been generated, further actions may be undertaken on the annotated image 514 to further inform a user of the controller of one or more parameters of the transferred aliquot of solution and/or the particles contained therein. In example embodiments, as shown in the example graphical user interface of FIG. 5D, a user may be presented with an annotated version of a single particle 520 in the solution, as well an annotated version of a multiple particles 522 that may be overlapping and/or joined together in the solution. In example embodiments, the user may select to generate one or more additional annotated images and/or graphical user interfaces based on the annotated image 514, including total particle counts in the sample, the types of particles in the sample, and the extent of overlapping particles in the sample, as well as results of the assay itself.

These example graphical user interfaces are merely for purposes of illustration. The features described herein may involve graphical user interfaces that are configured or formatted differently, include more or less information and/or additional or fewer instructions, include different types of information and/or instructions, and relate to one another in different ways.

EXAMPLES

To illustrate the example embodiments described above, several sample solutions were prepared and tested to measure the efficacy of the mixing speed and pipette depth of the shaker plate system. In example embodiments, these solutions may utilize a proprietary solution, a Phosphate Buffered Saline with Tween solution (PBS-T), some combination of the two, or other solutions. Additionally or alternatively, these solutions may also include a mixture of particles (e.g., bar coded paramagnetic beads) with a variety of different attributes (e.g., all bar coded paramagnetic beads may comprise a single bar code or a mix bar codes). Additionally, several solutions were prepared and tested to measure the efficacy of performing a read buffer phase. Further details are provided below.

Example 1: Read Buffer Phase

In an example experiment, paramagnetic bead solution was withdrawn and dispensed into a stationary dispense plate and then a dispense plate positioned on a Hamilton® Genomic STARlet shaker plate at a mix speed of 500 rpm. In both instances, 200 μL of read buffer solution was dispensed at a dispense rate of 300 μL per second (i.e., the total volume of the 200 μL of solution was dispensed into the vial in 0.666 seconds).

Figure 6A:
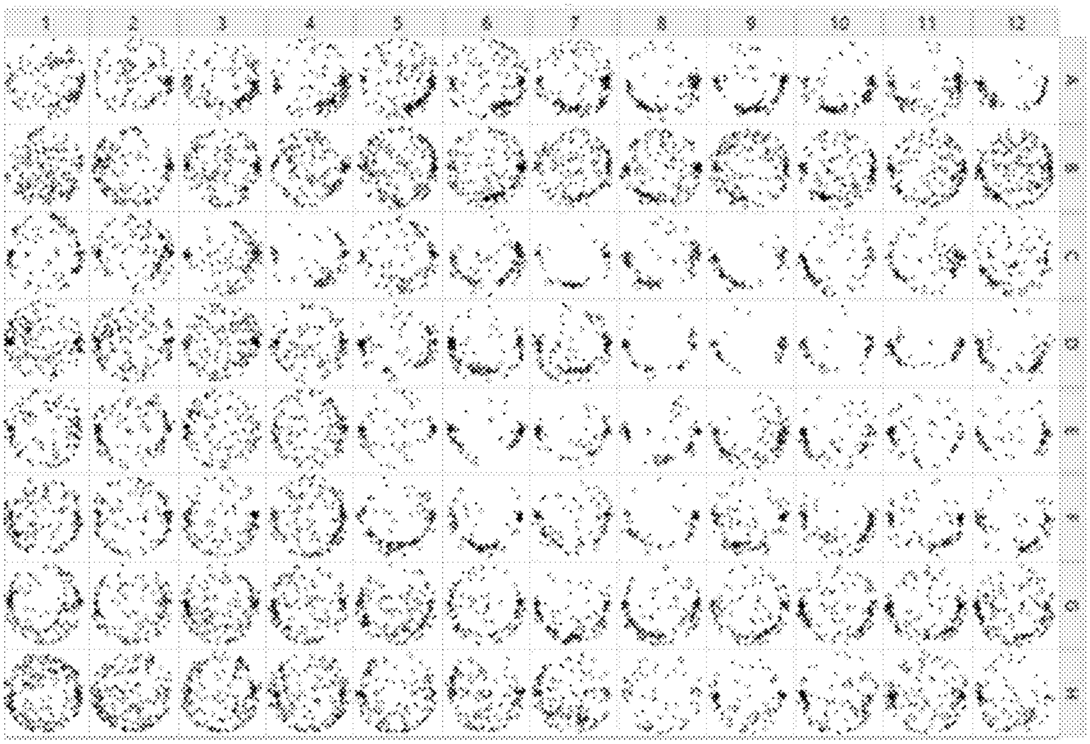
FIG. 6A illustrates particle count dispersion without a buffer solution phase.
Figure 6B:
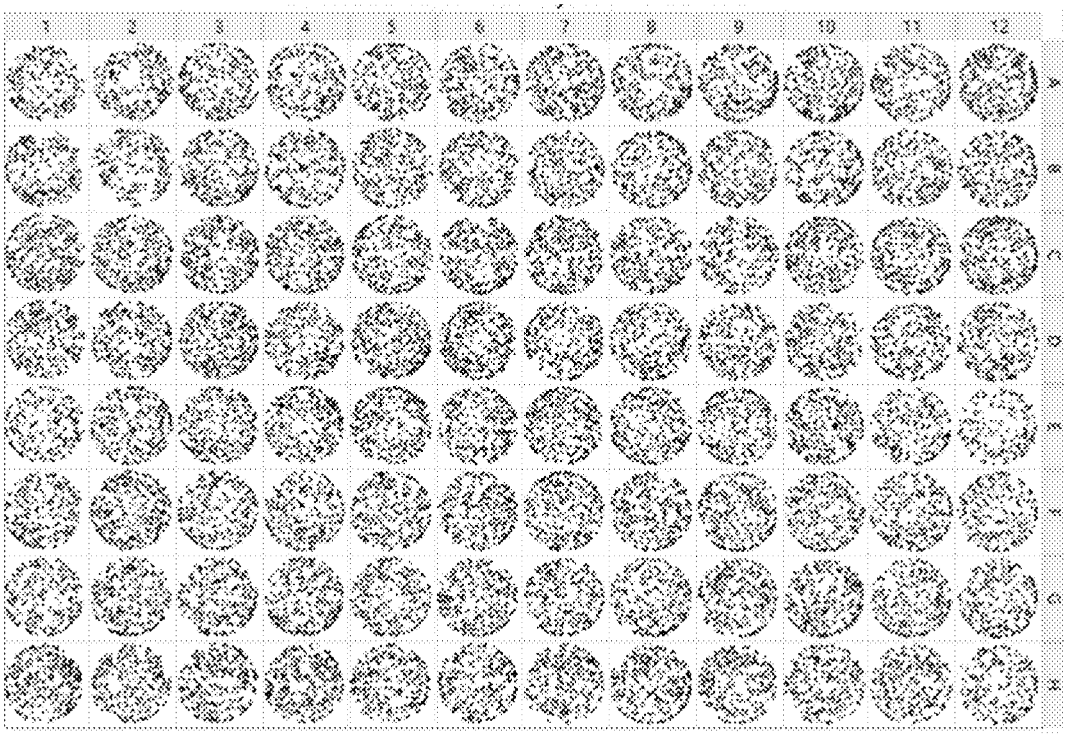
FIG. 6B illustrates particle count dispersion after conducting a buffer solution phase.

FIG. 6A shows the paramagnetic bead dispersion after the 200 μL of read buffer solution was dispensed in the vials on the stationary plate. FIG. 6B shows the paramagnetic bead dispersion after the 200 μL of read buffer solution was dispensed in the vials on the dispensing plate at a mixing speed of 500 rpm. By shaking the plate at 500 rpm, the read buffer solution was able to dispense into all locations of the interior well of the vials on the dispense plate and disperse the randomly placed paramagnetic beads in the total solution. In this regard, the total bead dispersion improved in the final solution, as did the results of the assay based on increased bead count. For example, as shown in FIG. 6A, with the stationary plate, 50% of the paramagnetic beads were counted in the assay. For comparison, in FIG. 6B, with the dispensing plate at a mixing speed of 500 rpm, 80% of the paramagnetic beads were counted in the assay.

Furthermore, although the experiment in Example 1 describes particular components and tests utilized according to specific parameters, it should be understood that the claimed devices and/or methods may be implemented in a variety of scenarios, including scenarios other than the assays described herein. For example, claimed devices and/or methods may be implemented in any situation where there is a need to pipette a consistently homogenous solution.

Example 2: Automated Bead Count

In an example experiment, using the devices, systems, or methods of FIGS. 5A-5D, a controller and associated program instructions to determine the accuracy of an automated bead counting protocol and compare it to a manual bead counting protocol. In the first portion of the experiment, an automated bead counting protocol was used to capture, stich, and analyze images of the sample solution to determine the total number (counts) of particles in the solution sample contained in a well (e.g., a Petri dish, a well, or the like). In a second portion of the example experiment, the sample solution was analyzed manually by an operator to determine the total number (counts) of particles in the solution sample contained in a well (e.g., a Petri dish, a well, or the like), by manually counting the particles in the captured images. After the first and second portions of the experiment, the counts were compared to determine an agreement between the automated and manual bead counting protocols.

Figure 6C:
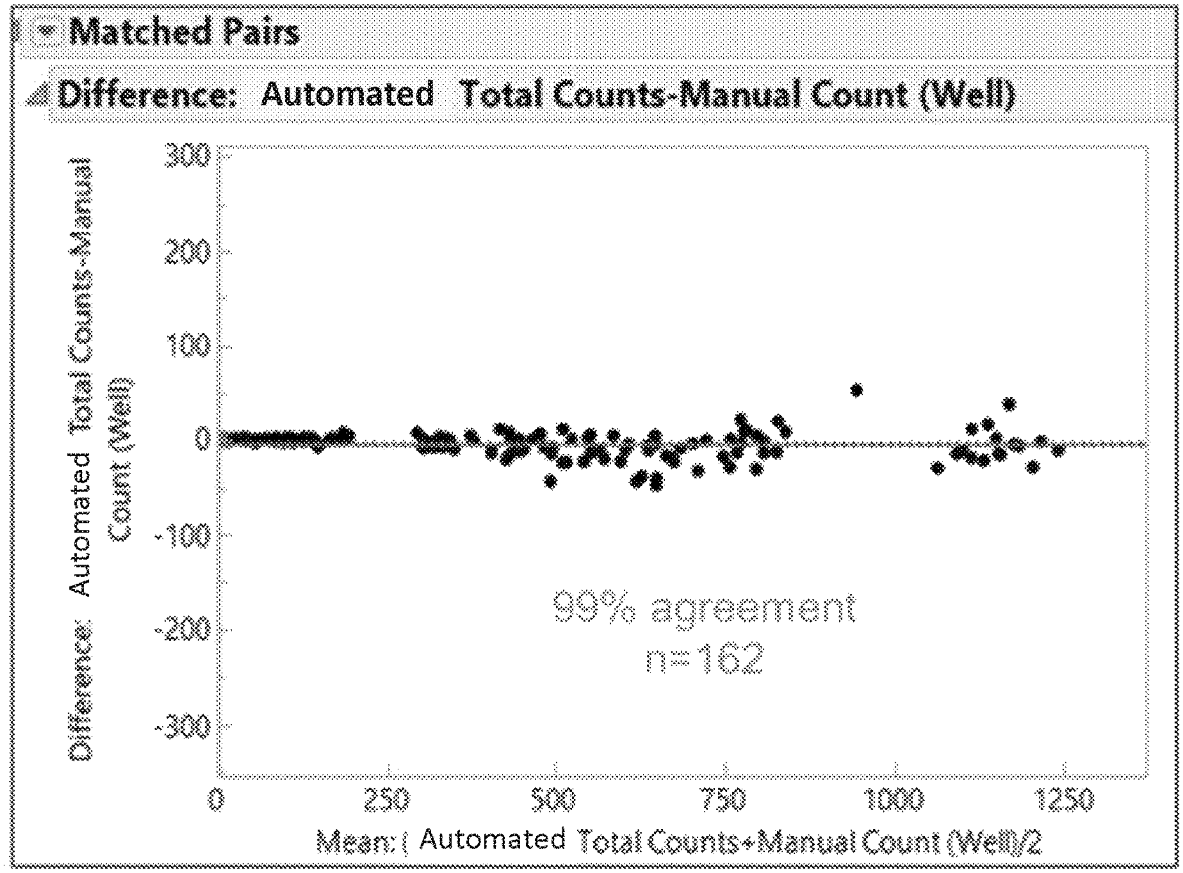
FIG. 6C illustrates particle count readings using an automated counting program compared to a manual counting protocol after a solution is prepared and an associated graphical user interface according to an example embodiment.

FIG. 6C shows the results of this experiment. Namely, FIG. 6C shows 99% agreement between the automated and manual bead counting protocols.

Additionally, utilizing automated bead counting protocols improved bead count consistency across image analysis, it also saves time in the overall bead counting protocol and solution preparation procedure, as well as ensures more consistent results in the solution preparation procedure. For example, because a user may efficiently and consistently test one or more parameters of the prepared solution (e.g., bead counts in representative samples of the prepared solution), the may user to increase the throughput (whether in an automated or manual procedure) and consistency of prepared solution, resulting in time and cost savings, as well as improved results, for the solution preparation (and assay) procedure.

Furthermore, although the experiment in Example 2 describes particular components and tests utilized according to specific parameters, it should be understood that the claimed devices and/or methods may be implemented in a variety of scenarios, including scenarios other than the solution preparation and/or assays described herein. For example, claimed devices and/or methods may be implemented in any situation where there is a need to prepare and/or pipette a consistently homogenous solution.

Example Methods and Aspects

Figure 7:
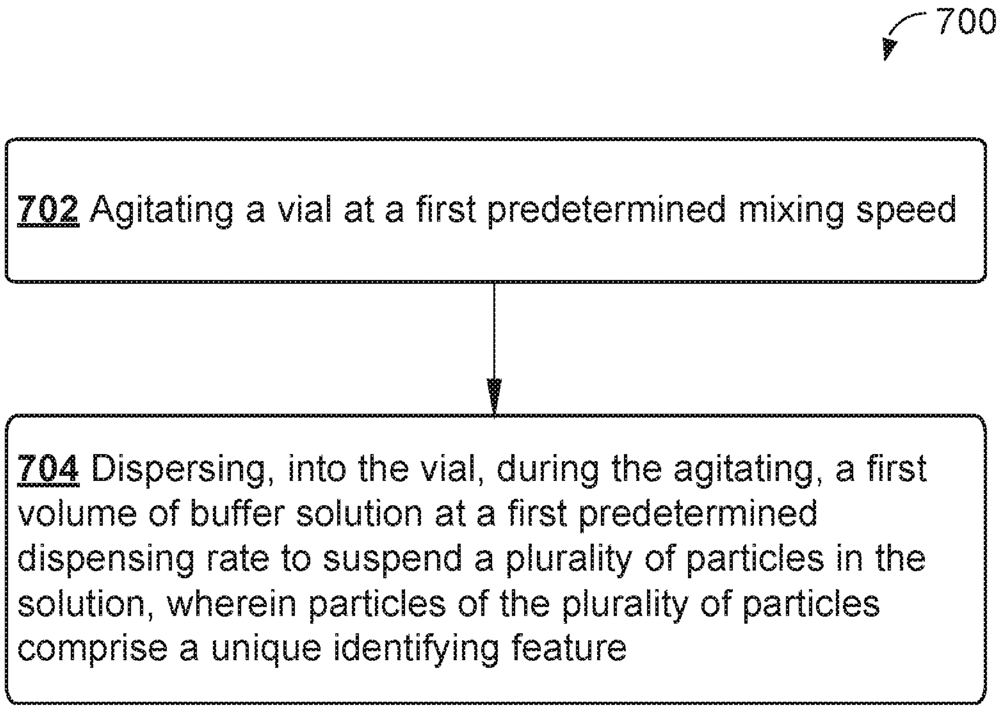
FIG. 7 illustrates a method, according to an example embodiment.

Now referring to FIG. 7, an example method of preparing a solution comprising a plurality of particles in a vial. Method 700 shown in FIG. 7 presents an example of a method that could be used with the components shown in FIGS. 1-6C, for example. Further, devices or systems may be used or configured to perform logical functions presented in FIG. 7. In other examples, components of the devices and/or systems may be arranged to be adapted to, capable of, or suited for performing the functions, such as when operated in a specific manner. Method 700 may include one or more operations, functions, or actions as illustrated by one or more of blocks 702-704. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

At block 702, method 700 for preparing a solution comprising a plurality of particles in a vial involves agitating the vial at a first predetermined mixing speed.

In some example embodiments, agitating the vial at the first predetermined mixing speed comprises moving the vial in an orbital pattern. In some examples, moving the vial in the orbital pattern comprises moving a center of the vial up to 3 millimeters from a horizontal center. Further, in some examples, the first predetermined mixing speed is between 400 revolutions per minute and 500 revolutions per minute. Alternatively, agitating the vial at the first predetermined mixing speed comprises moving the vial in a linear pattern.

At block 704, method 700 involves dispersing, into the vial, during the agitating, a first volume of buffer solution at a first predetermined dispersion rate to suspend the plurality of particles in the solution, wherein particles of the plurality of particles comprise a unique identifying feature.

In examples, the plurality of particles comprise a plurality of paramagnetic beads. Additionally, in some examples, the plurality of paramagnetic beads comprise two or more unique bar codes. In some examples, the plurality of particles further comprise a binding member corresponding to the unique identifying feature.

In examples, the first volume of buffer solution is between 180 microliters of buffer solution and 220 microliters of buffer solution. In some examples, the first predetermined dispersion rate is between 270 microliters of buffer solution per second and 330 microliters of buffer solution per second. In other examples, the first volume of buffer solution comprises 200 microliters of buffer solution, and wherein the first predetermined dispersion rate comprises 300 microliters of buffer solution per second.

In some examples, the buffer solution comprises a read buffer solution.

Additionally, in some examples, the method 700 further includes detecting, after the agitating and the dispersing, an assay read signal corresponding to at least one of the particles of the plurality of particles, wherein detecting the assay read signal occurs within a predetermined time period after completing the agitating and the dispersing.

Additionally, in some examples, the method 700 further includes transferring a sample of the prepared solution onto a surface, wherein the prepared solution comprises the first volume of buffer solution and the plurality of particles. In some examples, the method 700 further includes generating a composite image of the transferred sample of prepared solution, wherein the composite image comprises a plurality of images of the transferred sample of prepared solution. In other examples, the method 700 further includes, based on the generated composite image, determining a parameter of the transferred sample of prepared solution. In these examples, generating the composite image of the transferred sample of prepared solution further comprises stitching the plurality of images of the transferred sample of prepared solution into the composite image of the transferred sample of prepared solution. In other examples, determining a parameter of the transferred sample of prepared solution comprises counting the plurality of particles in the transferred sample of prepared solution. In still other examples, counting a plurality of particles in the transferred sample of prepared solution comprises detecting an edge of a particle in the composite image and, based at least in part on detecting an edge of the particle in the composite image, determining a presence of at least one particle in the composite image.

Additionally, in some examples, the method 700 further includes comparing the determined presence of at least one particle in the composite image to a previously generated image of the transferred sample of prepared solution. In these examples, the previously generated image of the transferred sample of prepared solution comprises one or more images of the transferred sample of prepared solution using ultraviolet light.

Additionally, in some examples, the method 700 further includes transmitting instructions that cause a graphical user interface to display a graphical representation of the determined parameter of the transferred sample of prepared solution.

In one aspect, a non-transitory computer-readable medium, having stored thereon program instructions that, upon execution by a controller, cause a controller to perform a set of operations comprising agitating a vial at a first predetermined mixing speed and dispersing, into the vial, during the agitating, a first volume of buffer solution at a first predetermined dispersion rate to suspend a plurality of particles in the prepared solution, wherein particles of the plurality of particles comprise a unique identifying feature, is disclosed.

The singular forms of the articles "a," "an," and "the" include plural references unless the context clearly indicates otherwise. For example, the term "a compound" or "at least one compound" can include a plurality of compounds, including mixtures thereof.

Various aspects and embodiments have been disclosed herein, but other aspects and embodiments will certainly be apparent to those skilled in the art. Additionally, the various aspects and embodiments disclosed herein are provided for explanatory purposes and are not intended to be limiting, with the true scope being indicated by the following claims.

What is claimed is:

1. A method for preparing a solution comprising a plurality of particles in a vial, the method comprising: agitating the vial comprising the plurality of particles at a first predetermined mixing speed; and dispersing, into the vial, during the agitating, a first volume of buffer solution at a first predetermined dispensing rate to suspend the plurality of particles in the solution to reduce binding of the plurality of particles to one another, wherein the first predetermined dispensing rate is between 270 microliters of buffer solution per second and 330 microliters of buffer solution per second, and wherein particles of the plurality of particles comprise a unique identifying feature.

2. The method of claim 1, wherein the plurality of particles comprises a plurality of paramagnetic beads.

3. The method of claim 1, wherein the unique identifying feature comprises one or more unique bar codes.

4. The method of claim 1, wherein particles of the plurality of particles further comprise a binding member corresponding to the unique identifying feature.

5. The method of claim 1, wherein agitating the vial at the first predetermined mixing speed comprises moving a vial in an orbital pattern.

6. The method of claim 5, wherein moving the vial in the orbital pattern comprises moving a center of the vial up to 3 millimeters from a horizontal center.

7. The method of claim 5, wherein the first predetermined mixing speed is between 400 revolutions per minute and 600 revolutions per minute.

8. The method of claim 1, wherein the first volume of buffer solution is between 180 microliters of buffer solution and 220 microliters of buffer solution.

9. The method of claim 1, wherein the first volume of buffer solution comprises 200 microliters of buffer solution, and wherein the first predetermined dispensing rate comprises 300 microliters of buffer solution per second.

10. The method of claim 1, wherein the buffer solution comprises a read buffer solution.

11. The method of claim 10, wherein the method further comprises: detecting, after the agitating and the dispersing, an assay read signal corresponding to at least one of the particles of the plurality of particles, wherein detecting the assay read signal occurs within a predetermined time period after completing the agitating and the dispersing.

12. The method of claim 1, wherein the method further comprises:

transferring a sample of the prepared solution onto a surface, wherein the prepared solution comprises the first volume of buffer solution and the plurality of particles;

generating a composite image of the transferred sample of prepared solution, wherein the composite image comprises a plurality of images of the transferred sample of prepared solution; and based on the generated composite image, determining a parameter of the transferred sample of prepared solution.

13. The method of claim 12, wherein generating the composite image of the transferred sample of prepared solution further comprises stitching the plurality of images of the transferred sample of prepared solution.

14. The method of claim 12, wherein determining a parameter of the transferred sample of prepared solution comprises counting the plurality of particles in the transferred sample of prepared solution.

15. The method of claim 14, wherein counting a plurality of particles in the transferred sample of prepared solution comprises:

detecting an edge of a particle in the composite image; and based at least in part on detecting an edge of the particle in the composite image, determining a presence of at least one particle in the composite image.

16. The method of claim 15, wherein the method further comprises:

comparing the determined presence of at least one particle in the composite image to a previously generated image of the transferred sample of prepared solution.

17. The method of claim 16, wherein the previously generated image of the transferred sample of prepared solution comprises one or more images of the transferred sample of prepared solution using ultraviolet light.

18. The method of claim 12, wherein the method further comprises: transmitting instructions that cause a graphical user interface to display a graphical representation of the determined parameter of the transferred sample of prepared solution.

19. A non-transitory computer-readable medium, having stored thereon program instructions that, upon execution by a controller, cause a controller to perform a set of operations comprising:

agitating a vial at a first predetermined mixing speed; and dispersing, into the vial, during the agitating, a first volume of buffer solution at a first predetermined dispensing rate to suspend a plurality of particles in a prepared solution to reduce binding of the plurality of particles to one another, wherein particles of the plurality of particles comprise a unique identifying feature.

* * * * *